(12) United States Patent
Ogg et al.

(10) Patent No.: US 10,351,847 B2
(45) Date of Patent: Jul. 16, 2019

(54) IDENTIFICATION AND DISPLAY OF PEPTIDE LIGANDS

(71) Applicant: OXFORD UNIVERSITY INNOVATION LIMITED, Oxford (GB)

(72) Inventors: Graham Ogg, Headington Oxford (GB); Li-Chieh Huang, Headington Oxford (GB); Terence Rabbitts, Headington Oxford (GB)

(73) Assignee: OXFORD UNIVERSITY INNOVATION LIMITED, Oxford (GB)

( * ) Notice: Subject to any disclaimer, the term of this patent is extended or adjusted under 35 U.S.C. 154(b) by 171 days.

(21) Appl. No.: 14/907,511

(22) PCT Filed: Jul. 23, 2014

(86) PCT No.: PCT/GB2014/052242
§ 371 (c)(1),
(2) Date: Jan. 25, 2016

(87) PCT Pub. No.: WO2015/011467
PCT Pub. Date: Jan. 29, 2015

(65) Prior Publication Data
US 2016/0298109 A1 Oct. 13, 2016

(30) Foreign Application Priority Data
Jul. 26, 2013 (GB) .................................. 1313352.5

(51) Int. Cl.
*C12N 15/10* (2006.01)

(52) U.S. Cl.
CPC .............................. *C12N 15/1075* (2013.01)

(58) Field of Classification Search
None
See application file for complete search history.

(56) References Cited

U.S. PATENT DOCUMENTS

| | | |
|---|---|---|
| 3,929,758 A | 12/1975 | Hughes et al. |
| 4,518,711 A | 5/1985 | Hruby et al. |
| 5,169,833 A | 12/1992 | Hansen, Jr. et al. |
| 5,216,124 A | 6/1993 | Hansen, Jr. et al. |
| 5,869,270 A | 2/1999 | Rhode et al. |
| 2004/0072262 A1 | 4/2004 | Montero-Jillian et al. |
| 2005/0019843 A1 | 1/2005 | Chen et al. |
| 2006/0110788 A1 | 5/2006 | Kudlicki et al. |
| 2006/0228758 A1 | 10/2006 | Muchal et al. |
| 2010/0136042 A1 | 6/2010 | Wong et al. |
| 2013/0303380 A1 | 11/2013 | Ogg et al. |
| 2015/0024958 A1* | 1/2015 | Derda ................ C12N 15/1037 506/9 |
| 2016/0341727 A1 | 12/2016 | Ogg et al. |

FOREIGN PATENT DOCUMENTS

| | | |
|---|---|---|
| EP | 1 452 868 A2 | 9/2004 |
| WO | 199108759 A1 | 6/1991 |
| WO | 199109051 A1 | 6/1991 |
| WO | WO 03/0161596 * | 7/2003 |
| WO | 2004077062 A3 | 9/2004 |
| WO | 2006009838 A2 | 1/2006 |
| WO | 2008013454 A2 | 1/2008 |
| WO | 2012022975 A1 | 2/2012 |
| WO | 2012057624 A1 | 5/2012 |

OTHER PUBLICATIONS

Uger et al (J. Immunol. 160:1598-1605) (Year: 1998).*
Ph.D.™ Phage Display Libraries Instruction Manual (downloaded from the internet Dec. 13, 2017).*
Li-Chieh Huang, et al., "Linking genotype to phenotype on beads: high throughput selection of peptides with biological function," Scientific Reports, vol. 3, Oct. 23, 2013 (Oct. 23, 2013), XP055159037, DOI 10.1038/srep03030 the whole document.
Rui Gan, et al., "Microbeads display of proteins using emulsion PCR and cell-free protein synthesis," Biotechnology Progress, vol. 24, No. 5, Sep. 1, 2008 (Sep. 1, 2008), pp. 1107-1114, XP55014985, ISSN: 8756-7938, DOI: 10.1002/btpr.43 abstract, figure 1.
S. Paul, et al., "Selection of a T7 promoter mutant with enhanced in vitro activity by a novel multi-copy bead display approach for in vitro evolution," Nucleic Acids Research, vol. 41, No. 1, Oct. 15, 2012 (Oct. 15, 2012), pp. e29-e29, XP055159046, ISSN: 0305-1048, DOI: 10.1093/nar/gks940, abstract figure 2.
Marc Ferrer, et al., "Peptide Ligands to Human Immunodeficiency Virus Type 1 gp120 Identified from Phage Display Libraries," Journal of Virology, Jul. 1, 1999 (Jul. 1, 1999), pp. 5795-5802, XP055159043, United States Retrieved from the Internet: URL:http://jvi.asm.org/content/73/7/5795, abstract.
International Search Report for corresponding PCT/GB2014/052242, dated Jan. 8, 2015 (3 pages).
Steen, H. et al., "The ABC's (and XYZ's) of Peptide Sequencing," Nature Reviews, Molecular Cell Biology, vol. 5, Sep. 2004, pp. 699-711.
Tawfik, D. et al., "Man-made cell-like compartments for molecular evolution," Research, Nature Publishing Group, vol. 16, pp. 652-656 (1998).
Lu, W. et al., In vitro selection of proteins via emulsion compartments, Methods, vol. 60, pp. 75-80 (2013).

(Continued)

*Primary Examiner* — Christopher M Gross
(74) *Attorney, Agent, or Firm* — Melissa Hunter-Ensor; Jana E. Harris; Greenberg Traurig, LLP

(57) ABSTRACT

A carrier to which is attached a peptide and DNA encoding the peptide, wherein the peptide includes at least one non-natural amino acid and/or wherein the peptide has a constrained secondary structure; or a carrier to which is attached β2 microglobulin, a peptide, and DNA encoding the peptide, said carrier not bearing an MHC or MHC-like molecule.

22 Claims, 12 Drawing Sheets
Specification includes a Sequence Listing.

(56) References Cited

OTHER PUBLICATIONS

Kojima, T. et al., "PCR amplification from single DNA molecules on magnetic beads in emulsion: application for high-throughput screening of transcription factor targets," Nucleic Acids Research, vol. 33, No. 17, pp. e150-3159 (2005).
Davidson, E. et al., "Directed Evolution of Proteins In Vitro Using Compartmentalization in Emulsions," Current Protocols in Molecular Biology, 24.6.1-24.6.12 (Jul. 2009).
Kelly, B.T. et al., "Miniaturizing chemistry and biology in microdroplets," ChemCommun., pp. 1773-1788 (2007).
Yang, H. et al., "Antiviral Inhibitory Capacity of CD8+ T cells Predicts the Rate of CD4+ T-Cell Decline in HIV-1 Infection," The Journal of Infectious Diseases, vol. 206, pp. 552-561 (2012).
Falciani, C. et al. "Bioactive Peptides from Libraries," Chemistry and Biology, vol. 12, No. 4, Apr. 1, 2005, pp. 417-426, XP055377937.
Gan, R. et al., "Microbeads Display of Proteins Using Emulsion PCR and Cell-Free Protein Synthesis," Biotechnol. Prog., vol. 24, pp. 1107-1114 (2008).
Paul, S. et al., "Selection of a T7 promoter mutant with enhanced in vitro activity by a novel multi-copy bead display approach for in vitro evolution," Nucleic Acids Research, vol. 41, No. 1, 11 pages (2013).
Lopez, J. et al., "High-throughput identification of T-lymphocyte antigens from Anaplasma marginale expressed using invitro transcription and translation," Journal of Immunological Methods, vol. 332, pp. 129-141 (2008).
Oved, K. et al., "Antibody-mediated targeting of human single-chain class I MHC with covalently linked peptides induces efficient killing of tumor or viral-specific cytotoxic T lymphocytes," Cancer Immunology, vol. 54, No. 9, pp. 867-879 (2005).
International Search Report for corresponding PCT Patent Application No. PCT/GB2011/051551, dated Jan. 24, 2012 (6 pages).
Joncker, N. et al., "Regulation of NK Cell Responsiveness to Achieve Self-Tolerance and Maximal Responses to Diseased Target Cells," Immunological Reviews, vol. 224, No. 1, pp. 85-87 (2008).
Mackensen, A. et al., "Phase I Study in Melanoma Patients of a Vaccine with Peptide-Pulsed Dendritric Cells Generated In Vitro from CD34+ Hematopoietic Progenitor Cells," International Journal of Cancer, vol. 86, No. 3, pp. 385-392 (2000).
Stone, J., et al., "HLA-restricted epitope indentification and detection of functional T cell responses by using MHC-peptide costimulatory microarrays," Proceedings of the National Academy of Sciences of USA, vol. 102, No. 10, p. 3744-3749 (2005).
Soen Y. et al., "Detection and Characterization of Cellular Immune Responses Using Peptide-MHC Microarrays," PLOS Biology, vol. 1, No. 3, pp. 429-438 (2003).
Borrego, F. et al., "Structure and function of major histocompatability complex (MCH) class I specific receptors expressed on human natural killer (NK) cells," Molecular Immunology, vol. 38, No. 9, pp. 637-660, Feb. 1, 2002.
Extended European Search Report received in corresponding European application No. 18213767.9, dated Mar. 8, 2019 (9 pages).

\* cited by examiner

Peptide library gene design

| T7 promoter | BZLF1 | Flexible linker | EBV lytic cycle protein BZLF1 (positive control), 18.51kD | linker | Human β2m | linker | Streptavidin binding protein | linker | T7 terminator |

| T7 promoter | Random epitope 9 a.a. | Flexible linker | Randomised epitope design, 18.51kD | linker | Human β2m | linker | Streptavidin binding protein | linker | T7 terminator |

NNN NNN NNN NNN NNN NNN NNN NNN NNN

Theoretically over $10^{18}$ randomness

FIG. 1B

| Test | Disulphide bond incorporation (normalised to kit positive/negative controls) |
|---|---|
| Negative control | 0 |
| 1 disulphide bridge | 51% |
| 2 disulphide bridges | 100% |

IDENTIFICATION AND DISPLAY OF PEPTIDE LIGANDS

This invention relates to the identification of peptide ligands and the DNA encoding the peptide ligands. The invention also relates to carriers for use in the identification of peptide ligands and for the display of peptide ligands.

SEQUENCE LISTING

The instant application contains a Sequence Listing which has been submitted electronically in ASCII format and is hereby incorporated by reference in its entirety. Said ASCII copy, created on May 3, 2016, is named 368908.1000US1 (00001)SL.txt and is 7304 bytes in size.

Peptides ligands represent important biological molecules in vivo and indeed several peptides have been taken forward into therapeutic use. However uptake of therapeutic peptide technology has been slow compared to antibody therapeutics despite advantages in cost, tissue penetration and possible non-parenteral route of administration (e.g. inhaled). This is related to a number of problems including the difficulty of screening for peptides of interest from libraries because of their relative low affinity in linear conformation. Secondly, conventional peptide libraries generated using F-moc chemistry are prohibitively expensive for the library sizes required for drug discovery. Thirdly, problems have included peptide stability in vivo. Stability problems may be improved by the use of non-natural/unnatural amino acids or structured/stapled peptides e.g. ciclosporin, or other conjugations e.g. pegylation.

With the continued need for drug discovery and the continued quest to understand disease and infection, there remains a need for improved methods to study protein:protein interactions and to identify potential protein ligands for molecules e.g. receptors. There are currently numerous methods available to study protein interactions and to screen for potential ligands, these include, but are not limited to, affinity chromatography, phage display, the yeast two hybrid system, protein microarrays and 3D structural analysis using X-ray crystallography and/or NMR.

Ideally, the mechanism of probing protein interactions or probing for potential ligands will directly link any identified protein or peptide to its encoding DNA. The advantage of linking the peptide to the encoding DNA is that methods available to sequence the DNA are far more sophisticated than those available to sequence protein. In particular, DNA sequencing is much more rapid and is cheaper than protein sequencing. DNA sequencing can be successful on very small samples—small in both length and molar amounts. Furthermore, DNA samples can be easily amplified to provide more DNA if needed. DNA sequencing can be undertaken by traditional Sanger based methodology or by various high throughput sequencing approaches (Sequencing technologies—the next generation. Metzker M L. Nat Rev Genet. 2010 January; II (I): 31-46, the contents of which is hereby incorporated by reference in its entirety). In contrast, protein sequencing can be via Edman degradation or through mass spectrometry approaches (Hanno Steen & Matthias Mann. The abc's (and xyz's) of peptide sequencing. Nature Reviews Molecular Cell Biology, 5:699-711, 2004, the contents of which is hereby incorporated by reference in its entirety).

Existing approaches that are amenable to protein library screening and that link genotype to phenotype include phage-display, yeast-display, ribosomal and mRNA displays. The latter in vitro library approaches are challenging for peptides as it is difficult to multiplex expressed peptides to the numbers required for detection of low affinity interactions. In contrast, the in vivo methods of phage and yeast display allow multiplexing of proteins or peptides on the surface, but they share the same disadvantage that in addition to the proteins under study there are other proteins that are on both the phage and/or the yeast which can interfere with binding. This can lead to non-specific interactions which can be difficult to distinguish from interactions of interest which is particularly problematic for peptide screening. Furthermore, these methods commonly use coat fusion proteins which can alter the conformation of both interacting partners and influence binding. The produced proteins may be toxic to the yeast or the phage or influence their replication which can select out library bias. The use of unnatural amino acids and post-translational modifications may provide significant affinity and stability advantages and these are difficult to achieve using phage or yeast during the selection step. Lastly, in vivo systems have associated limitations in library size that can be overcome using in vitro expression systems. Tawfik and Griffiths and colleagues established emulsion micro-compartments as a means to isolate reactions (Tawfik, D. S. and A. D. Griffiths, *Man-made cell-like compartments for molecular evolution.* Nat Biotechnol, 1998. 16(7): p. 652-6, the contents of which is incorporated by reference). It was reported that in a 1 ml reaction volume, more than $10^{10}$ water-in-oil emulsion micro-compartments can be created, with each having a mean diameter in the range of 2-3 μm and mean volume of 5 femtoliters. At this volume, a single molecule achieves a concentration of approximately 0.5 nM, thus enabling a single DNA molecule to be transcribed and translated. With appropriate dilution of DNA molecules, it is possible to create individual water-in-oil emulsions in which only one DNA molecule is present in a microcompartment, and the protein expressed is trapped in a single confined physical space, i.e. creating $10^{10}$ unique directed evolution reactions. Compared to the current library display technology, emulsions provide the convenience of a cell-free environment, preventing the interference of toxic substrates or unwanted cellular interactions (Lu, W. C. and A. D. Ellington, *In vitro selection of proteins via emulsion compartments.* Methods, 2012, the contents of which are herein incorporated by reference). Nakano and colleagues extended the technology to combine emulsion PCR with emulsion in vitro transcription/translation, to generate beads combining protein and the DNA encoding the said protein. Beads binding to the selected target were obtained using flow cytometric guided cell sorting and multiple rounds of selection and bead re-derivation (Kojima, T., et al., *PCR amplification from single DNA molecules on magnetic beads in emulsion: application for high-throughput screening of transcription factor targets.* Nucleic Acids Res, 2005. 33(17): p. e150; Gan, R., et al., *Microbeads display of proteins using emulsion PCR and cell-free protein synthesis.* Biotechnol Prog, 2008. 24(5): p. 1107-14; and Paul, S., et al., *Selection of a T7 promoter mutant with enhanced in vitro activity by a novel multi-copy bead display approach for in vitro evolution.* Nucleic Acids Res, 2012, the contents of all of which are incorporated by reference). However flow cytometric based approaches associate with loss of sensitivity and specificity secondary to the requirement to express threshold levels of fluorescence before selection which is not amenable to linear peptide selection with relative low affinity.

The search for peptide ligands often focuses on finding ligands with high binding affinity to the molecule/receptor of interest. However, there is a risk that screening or selection techniques which are optimised for the discovery of high affinity ligands will overlook or exclude lower affinity ligands which may, notwithstanding their low affinity, provide the desired biological activity (for example agonistic or antagonistic activity).

An aim of the present invention is therefore to provide an improved system to screen for and select peptide ligands, in particular to screen for and select low affinity ligands, and/or to screen for and select ligands containing non-natural or modified amino acids, and/or to screen or select for ligands having a constrained secondary structure.

According to a first aspect, the invention provides a carrier to which is attached a peptide and DNA encoding the peptide. In a first aspect of the invention, the peptide includes at least one non-natural amino acid, and/or has a constrained secondary structure.

By non-natural amino acids is meant any amino acid that is not considered by those skilled in the art as a proteinogenic or 'natural' amino acid, normally encoded by the genetic code. The natural amino acids excluded by the term 'non-natural amino acids are: L-alanine, L-arginine, L-asparagine, L-aspartic acid, L-cysteine, L-glutamic acid, L-glutamine, L-glycine, L-histidine, L-isoleucine, L-leucine, L-lysine, L-methionine, L-phenylalanine, L-proline, L-serine, L-threonine, L-tyrptophan, L-tyrosine and L-valine.

Any non-natural amino acid may be incorporated into the peptide.

Peptides attached to carriers of the invention which incorporate non-natural amino acids may be synthesised by in vitro translation, and preferably by in vitro transcription/translation (IVTT) from the DNA carried on the carrier. Most preferably, the peptides are synthesised by emulsion IVTT. In vitro translation allows for the use of modified tRNA species carrying modified or non-natural amino acids, and may take advantage of, for example, known amber, ochre or opal stop codon suppressor tRNA technologies. Alternative technologies for incorporation of non-natural amino acids include engineered amino acid-tRNAs that recognise four-base codons. Other technologies will be apparent to those skilled in the art.

In peptides which have a constrained structure, the peptide conformation is restricted by the formation of a linkage at at least two different amino acid sites. Preferably, the conformation is restricted by the formation of at least one internal bond within the peptide. Preferably, the internal bond comprises an SS-bridge and/or an alternative linkage. Alternatively, or in addition, the constrained conformation may be created by binding the peptide to a scaffold and/or a carrier. The peptide may be attached to a scaffold and/or carrier via at least two linkages. Methods and reagents for preparing peptides with constrained secondary structure are know from, for example. EP 1452868, WO2004077062, WO2008013454 and WO2012057624, the contents of each of which being incorporated herein by reference in their entirety.

Where the peptide includes an internal bond, the internal bond preferably comprises a disulphide bond. Disulphide bonds are selectively formed between free cysteine residues without the need to protect other amino acid side chains. Furthermore, disulphide bonds are easily formed by incubating in a basic environment. Preferably a disulphide bond is formed between two cysteine residues, since their sulfhydryl groups are readily available for binding. The location of an SS-bridge within an amino acid sequence is easily regulated by regulating the location of free cysteine residues. In a particularly preferred embodiment said cysteines are located around the first and last amino acid position of the amino acid sequence, in order to optimally restrict the conformation of the amino acid sequence.

Other kinds of internal bonds are also suitable for restricting the conformation of the peptides. For instance, Se—Se diselenium bonds may be used. An advantage of diselenium bonds is that these bonds are reduction insensitive. Peptides comprising a diselenium bond are better capable of maintaining their conformation under reducing circumstances. Alternatively, or additionally, a metathese reaction is used in order to form an internal bond. In a metathese reaction two terminal CC-double bonds or triple bonds are connected by means of a Ru-catalysed rearrangement reaction. Such terminal CC-double or CC-triple bonds are for instance introduced into a peptide either via alkylation of the peptide NH-groups, for instance with allyl bromide or propargyl bromide, or via incorporating a non-natural amino acid with an alkenyl- or alkynyl-containing side chain into the peptide. A metathese reaction is performed with a Grubbs-catalyst.

In one embodiment an internal bond is formed using Br—SH cyclisation. For instance, an SH moiety of a free cysteine is coupled to a BrAc-moiety which is preferably present at the N-terminus of the peptide or at a lysine (RNH$_2$) side chain.

In a further embodiment a COOH-side chain of an aspartate or glutamate residue is coupled to the NH$_2$-side chain of a lysine residue. This way an amide bond is formed. It is also possible to form an internal bond by coupling the free COOH-end of a peptide to the free NH$_2$-end of the peptide, thereby forming an amide-bond. Alternative methods for forming an internal bond within an amino acid sequence are available, which methods are known in the art.

In some embodiments, the peptides are constrained by binding to a scaffold. Various procedures to obtain monocyclic peptides are known. Various efficient synthetic routes to scaffolds for preparing monocyclic peptides have been developed, along with methods for their incorporation into peptidomimetics using solid-phase peptide synthesis. Among the various approaches utilized for preparing monocyclic peptides, several employ peptides containing pairs of cysteine residues allowing subsequent cyclization via disulfide bond formation (see e.g. U.S. Pat. Nos. 3,929,758; 4,518,711; 526,124; 5,169,833; 4,518,711; WO9109051; WO9108759, the disclosures of each of which are herein incorporated by reference in their entirety).

A preferred example peptides with two free cysteine thiols that react rapidly with a variety of scaffold molecules are bound to the carrier. In one embodiment, a synthetic scaffold comprising at least two identical reactive groups is used to couple one or more potential binding site molecules, e.g. peptides or peptide fragments, to said scaffold. Suitable peptides comprise all possible peptides capable of reacting with at least two reactive groups on a scaffold to form at least two linkages or bonds between the peptide and the scaffold The scaffold may comprise a (hetero) aromatic molecule with at least a first and a second reactive group as disclosed in WO 2004/077062, preferably a (hetero)aromatic molecule comprising at least two benzylic halogen substitutents. The two benzylic halogen substitutents are preferably used as first and second reactive group for coupling an amino acid sequence. An amino acid sequence is preferably coupled to a scaffold using a method according to WO 2004/077062. Briefly, a scaffold with at least a first and a second reactive group is provided. An amino acid sequence capable of reacting with said at least first and second reactive group is contacted with said scaffold under conditions allowing said amino acid sequence to react with said at least first and second reactive group to form at least two linkages between said scaffold and said amino acid sequence, wherein the formation of a first linkage accelerates the formation of a consecutive linkage. This way, conformationally constrained loop constructs are formed. An advantage of the methods and scaffolds according to WO 2004/077062 is the fact that amino acid sequences are coupled to these scaffolds in a fast, simple and straightforward way. With a method as disclosed in WO 2004/077062 it has become possible to use unprotected peptides. Hence, laborious protection and deprotection steps are not necessary. Furthermore, the scaffolds need not be selectively functionalized. Moreover, the coupling reaction using a scaffold as disclosed in WO 2004/077062 is suitable for being performed in solution. An amino acid sequence is preferably coupled to a scaffold using a method according to WO 2004/077062 in an aqueous solution, thereby limiting or even avoiding the use of (toxic) organic solvents.

Since the formation of a first linkage accelerates the formation of a second linkage, the attachment of an amino acid sequence to a scaffold according to WO 2004/077062 takes place in a rapid, concerted process comprising a cascade of reactions. The formation of a first linkage via a first reactive group increases the reactivity of a second reactive group, and so on, such that the activating effect is being 'handed over' from one reactive group to the next one. Said chemical reactions involve changes at functional groups while the molecular skeleton of the scaffold remains essentially unchanged. For example, a scaffold molecule as used in WO 2004/077062 comprising at least two reactive groups is capable of reacting with an amino acid sequence such that the reactive groups of the scaffold become involved in the new linkages with the amino acid sequence while the core structure or skeleton of the scaffold does not participate directly in the coupling.

Most preferably the scaffold comprises: a halogenoalkane, preferably a dihaloalkane, a trihaloalkane or a tetrahaloalkane; and/or an allylic system, preferably a scaffold comprising two allylic halogen atoms; and/or a scaffold comprising at least two halomethyl groups; and/or a (hetero) aromatic molecule, preferably a (hetero)aromatic molecule comprising at least two benzylic halogen substitutents.

In one embodiment, a scaffold comprises a conjugated polyene, also known as aromatic compound, or arene, which is provided with at least two reactive groups. Preferably, a molecular scaffold is used which comprises at least two benzylic halogen substituents, such as halomethyl groups. Suitable examples include, but are not limited, to di (halomethyl) benzene, tri (halomethyl) benzene or tetra (halomethyl) benzene and derivatives thereof.

Preferably, the scaffold comprises a halogenoalkane. Halogenoalkanes (also known as haloalkanes or alkyl halides) are compounds containing a halogen atom (fluorine, chlorine, bromine or iodine) joined to one or more carbon atoms in a chain. Also preferred are dihaloscaffolds, comprising two halogen atoms, and tri- and tetrahaloscaffolds for the synthesis of conformationally constraint compounds, like for example peptide constructs consisting of one or more looped peptide segments. Other prefered scaffolds comprise a halomethylarene, preferably selected from the group consisting of bis(bromomethyl)benzene, tris(bromomethyl)benzene and tetra(bromomethyl)benzene, or a derivative thereof. More preferably said scaffold is selected from the group consisting of ortho-, meta- and para-dihaloxyleen and 1,2,4,5 tetra halodurene. Said scaffold most preferably comprises meta-1,3-bis(bromomethyl)benzene (m-T2), ortho-I,2-bis(bromomethyl)benzene (o-T2), para-I,4-bis(bromomethyl)benzene (p-T2), meta-I,3-bis(bromomethyl)pyridine (m-P2), 2,4,6-tris(bromomethyl)mesitylene (T3), meta-I,3-bis(bromomethyl)-5-azidobenzene (m-T3-N3) and/or 1,2,4,5 tetrabromodurene (T4).

Preferably the scaffold is for example selected from the group consisting of bis-; tris-; or tetra(halomethyl)benzene; bis-; tris-; or tetra(halomethyl)pyridine; bis-; tris-; or tetra (halomethyl)pyridazine; bis-; tris-; or tetra(halomethyl)pyrimidine; bis-; tris-; or tetra(halomethyl)pyrazine; bis-; tris-; or tetra(halomethyl)-1,2,3-triazine; bis-; tris-; or tetra(halomethyl)-1,2,4-triazine; bis-; tris-; or tetra(halomethyl)pyrrole, -furan, -thiophene; bis-; tris-; or tetra(halomethyl) imidazole, -oxazole, -thiazol; bis-; tris-; or tetra (halomethyl)-3H-pyrazole, -isooxazole, -isothiazol; bis-; tris-; or tetra(halomethyl)biphenylene; bis-; tris-; or tetra (halomethyl)terphenylene; 1,8-bis(halomethyl)naphthalene; bis-; tris-; or tetra(halomethyl)anthracene; bis-; tris-; or tetra(2-halomethylphenyl)methane; or, if applicable, another regioisomer thereof. For example, 1,2-bis(halomethyl)benzene; 3,4-bis(halomethyl)pyridine; 3,4-bis(halomethyl) pyridazine; 4,5-bis(halomethyl)pyrimidine; 4,5-bis(halomethyl)pyrazine; 4,5-bis(halomethyl)-1,2,3-triazine; 5,6-bis (halomethyl)-1,2,4-triazine; 3,4-bis(halomethyl)pyrrole, -furan, -thiophene and other regioisomers, 4,5-bis(halomethyl)imidazole, -oxazole, -thiazol; 4,5-bis(halomethyl)-3H-pyrazole, -isooxazole, -isothiazol; 2,2'-bis(halomethyl)biphenylene; 2,2"-bis(halomethyl)terphenylene; 1,8-bis (halomethyl)naphthalene 1,10-bis(halomethyl)anthracene; bis(2-halomethylphenyl)methane; 1,2,3-tris(halomethyl) benzene, 2,3,4-tris(halomethyl)pyridine; 2,3,4-tris(halomethyl)pyridazine; 3,4,5-tris(halomethyl)pyrimidine; 4,5,6-tris(halomethyl)-1,2,3-triazine; 2,3,4-tris(halomethyl) pyrrole, -furan, -thiophene; 2,4,5-bis(halomethyl)imidazole, -oxazole, -thiazol; 3,4,5-bis(halomethyl)-1H-pyrazole, -isooxazole, -isothiazol; 2,4,2'-tris(halomethyl)biphenylene; 2,3',2"-tris(halomethyl)terphenylene; 1,3,8-tris(halomethyl) naphthalene 1,3,10-tris(halomethyl)anthracene; bis(2-halomethylphenyl)methane; 1,2,4,5-tetra(halomethyl)benzene; 1,2,4,5-tetra (halomethyl)pyridine; 2,4,5,6-tetra (halomethyl)pyrimidine; 2,3,4,5-tetra(halomethyl)pyrrole; -furan; -thiophene; 2,2',6,6'-tetra(halomethyl)biphenylene; 2,2",6,6"-tetra(halomethyl)terphenylene 2,3,5,6-tetra(halomethyl)naphthalene and 2,3,7,8-tetra(halomethyl)anthracene; Bis(2,4-bis(halomethyl)phenyl)methane.

Embodiments in which a non-natural amino acid is incorporated into the peptide, and/or in which the peptide has a constrained secondary structure may further include any of the features described herein with reference to a second aspect of the invention. In particular the use of linkers and the incorporation of binding pair members and β2 microglobulin, as described herein may be employed equally for this first aspect of the invention as for the second aspect described below.

In a second aspect, the invention provides a carrier to which is attached β2 microglobulin, a peptide and DNA encoding the peptide, said carrier not bearing an MHC or MHC-like molecule.

In either the first or the second aspect of the invention, the carrier may further include a flexible linker attached to the peptide, e.g. a flexible peptide linker. A flexible peptide linker is series of amino acids which connects two defined regions, such as the peptide and the β2 microglobulin, and allows the two defined regions to move. Preferably the linker allows the two regions to have locational freedom. Preferably the linker allows the regions it links to form their preferred configuration whilst still being linked.

In some embodiments of the first aspect the carrier further comprises β2 microglobulin attached to the peptide. In some embodiments the β2 microglobulin provides the flexible peptide linker function.

In some embodiments the carrier further comprises, a tag e.g. a His tag, a hapten, an epitope, a binding fragment of an antibody or another member of a binding pair, such as a streptavidin binding protein. In some embodiments such further peptide sequences provide the flexible peptide linker function. One or more such peptide sequences may be provided.

Where included in embodiments of the first aspect, and in the second aspect, the β2 microglobulin may be attached to the carrier, either directly or via the peptide, or may be located at the carrier surface but not physically attached.

In the second aspect, the β2 microglobulin is provided on the carrier in the absence of an MHC or MHC-like molecule, which, surprisingly, is not required for the presentation of the peptide in the invention. Accordingly, the carrier does not bear or carry an MHC or MHC-like molecule.

Where the β2 microglobulin is attached to the carrier via the peptide, it may be constructed as a fusion with the peptide, and the DNA may encode the β2 microglobulin-peptide fusion. Alternatively the β2 microglobulin may be provided exogenously.

The peptide, or the β2 microglobulin-peptide fusion, may be attached to the carrier by means of an interaction between members of a binding pair of molecules. In some embodiments, one of the members of a binding pair is attached to the peptide or fusion and the second member is attached directly or indirectly (e.g. via a linker) to the carrier. Several binding pairs are known to the skilled person, and any may be used in order to immobilise the peptide on the carrier. Most conveniently, and particularly where the peptide is created using in vitro transcription/translation (IVTT) from the DNA on the carrier, the binding pair member attached to the peptide or fusion is a proteinaceous member that can be expressed as a fusion protein with the peptide or as a fusion with the β2 microglobulin-peptide fusion.

For example, the binding member attached to the peptide or fusion may be a streptavidin binding protein. The peptide may therefore be configured to be expressed from the DNA on the carrier as a streptavidin binding protein-peptide fusion, or in other embodiments as a streptavidin binding protein-β2 microglobulin-peptide fusion. Preferably, in such a fusion, the β2 microglobulin will be adjacent to the peptide and will separate the peptide from the streptavidin binding protein. One or more flexible linkers may be provided between any of the components of the fusion. For example in one embodiment, the fusion may comprise, in order: streptavidin binding protein-flexible linker-β2 microglobulin-flexible linker-peptide. Other arrangements of fusion proteins containing the desired components will be apparent to the skilled person.

In other embodiments, the binding partner attached to the peptide or β2 microglobulin-peptide fusion may be a binding fragment of an antibody, such as a scFv, a dAb, VL or VH domain. The binding fragment may be arranged as a fusion protein with the peptide or β2 microglobulin-peptide fusion in the same ways as discussed above in relation to streptavidin binding protein.

Where streptavidin binding protein is attached to the peptide or β2 microglobulin-peptide fusion, streptavidin is attached to the carrier either directly or indirectly (e.g. via a linker). Expression of the peptide or β2 microglobulin-peptide fusion, attached (e.g. as a further fusion) to streptavidin binding protein will result in binding of the streptavidin binding protein to the streptavidin and consequent immobilisation of the peptide on the carrier.

Similarly, where the binding fragment of an antibody is attached to the peptide or β2 microglobulin-peptide fusion, the cognate antigen or hapten is attached to the carrier either directly or indirectly (e.g. via a linker). Expression of the peptide or β2 microglobulin-peptide fusion, attached (e.g. as a further fusion) to binding fragment of an antibody will result in binding of that binding fragment to the antigen or hapten, and consequent immobilisation of the peptide on the carrier.

In yet further embodiments, a binding fragment of an antibody (including fragments having more than one chain, such as F(ab), F(ab')$_2$, F(ab')) or a whole antibody may be immobilized on the carrier and the antigen or hapten may be attached to the peptide or β2 microglobulin-peptide fusion. Where the antigen or hapten is a peptide it may be expressed as part of a fusion with the peptide or β2 microglobulin-peptide fusion in multiple configurations, as discussed above for streptavidin binding protein.

Preferably the carrier is multivalent. Preferably multiple copies of both the peptide and the encoding DNA are attached, preferably at least 10, 100, 1000 or more copies of either the peptide and/or the DNA are attached.

The peptide attached to the carrier in any of the embodiments described herein may be between about 4 and about 50 amino acids in length, preferably the peptide is between about 4 and 20 amino acids, preferably between about 7 and about 15 amino acids, preferably the peptide is between about 7 and about 12 amino acids, preferably the peptide is between about 8 and about 12 amino acids, preferably the peptide is between about 8 and about 10 amino acids, preferably the peptide is about 9 amino acids, preferably the peptide is 9 amino acids.

The peptide may be randomly generated or derived from a source library, for example, from a particular human or non-human cell type.

In preferred embodiments and uses of the carriers of the invention, at least two peptides are presented on carriers for screening or selection of peptide ligands for molecules. Accordingly the invention further provides a library containing a plurality of carriers as described herein, wherein the library contains at least two different peptides borne on separate carriers. Preferably the set of peptides in the library contains peptides including variable amino acids in order to provide a range of peptides that differ at one or more amino acid positions. Accordingly in some embodiments the library contains a set of peptides in which at least one amino acid position is variable. In some embodiments the variation at the at least one amino acid position is limited and determined by the user of the invention. In other embodiments the variation is random, allowing for the creation of a random library. Variation or randomisation of an amino acid position can be comprehensive to include all possible natural amino acids at that position within the set, or may be less comprehensive so that within the set only a subset of possible amino acids are present at the variable or randomised position or positions. In other embodiments, variability or randomisation may be extended to include non-natural amino acids at the variable or randomised position or positions. Where the peptide ligands within the library include peptides having a constrained secondary structure, the nature and extent of the constraint may also be varied or randomised within the library.

Preferably more than one amino acid position in the peptide is variable to some degree. Accordingly, in some embodiments at least 2, 3, 4, 5, 6, 7, 8, 9 or 10 amino acid positions, or all amino acid positions of the peptide are varied or randomised. The number of varied or randomised positions and the degree of variation or randomisation has an impact on the size of the resultant library and the skilled person will be aware of the theoretical maximum size of the library, calculated from these factors. In some instances, theoretical maximum sizes of libraries may not be achievable where such library sizes exceed the practical capabilities of manufacture or handling. Nonetheless, in embodiments in which the theoretical maximum library size cannot be achieved due to physical restraints, it may still be advantageous to use such a high degree of diversity (that is a large number of varied or randomised positions and a high degree of variation or randomisation). In such circumstances a resultant library may contain only a subset of the theoretical maximum diversity.

The carrier may be a solid support. The solid support may be a column, a plate surface (such as the surface of a tissue culture plate or the surface of a multiwell plate), a bead or any other suitable support. If the carrier is a bead, the bead may be of any polymeric material, such as polystyrene, although non-polymeric materials, such as silica, may also be used. Other materials which may be used include styrene copolymers, methyl methacrylate, functionalised polystyrene, glass, silicon, and carboxylate. Optionally the beads may be magnetic, which facilitates their isolation after being used in reactions.

Preferably the beads are microspheres with a diameter from about 0.1 to about 10 microns. The beads may alternatively be any small discrete particle they need not be spherical in shape. Preferably they will be similar in size to a sphere of about 0.1 to about 10 microns, but different sized structures including nanometer sized particles may also be used.

Optionally the beads may be selected from Dynabead C1, M270 or MACS.

Preferably each bead carries multiple copies of the same peptide and the same DNA encoding the peptide. The number of copies may range from about 2 to a million or more. Preferably there are at least 10 copies, at least 20 copies, at least 50 copies, at least 100 copies, at least 500 copies, at least 1000 copies, at least 10,000 copies, at least 100,000 copies. Preferably only one peptide species and only one DNA species is found on each bead. The method of the invention may use multiple beads wherein different beads have different peptides and DNA sequences attached.

In a preferred embodiment, in vitro transcription/translation (IVTT) is used to produce the peptide and/or the β2 microglobulin, which is bound to the carrier surface. The peptide and β2 microglobulin may be synthesised by IVTT as a single linked product. In some embodiments, the peptide is fused via a peptide bond to a terminal amino acid of the β2 microglobulin to create a fusion protein. The peptide may be fused at the C-terminal or N-terminal end of the β2 microglobulin.

In alternative embodiments, the peptide can be fused at an internal site in the β2 microglobulin, in particular within an external loop. The positions of external loops can be predicted by in-silico processing and imaging (see FIG. 8).

Accordingly, in some embodiments the peptide is fused to the β2 microglobulin in loop 1 between about amino acids 10 and 20. In other embodiments, the peptide is fused to the β2 microglobulin in loop 2 between about amino acids 30 and 35. In other embodiments the peptide is fused to the β2 microglobulin in loop 3 between about amino acids 70 and 78. In other embodiments the peptide is fused to the β2 microglobulin in loop 4 between about amino acids 83 and 91 (reference to amino acid numbering is to the sequence of the mature β2 microglobulin protein as provided in FIG. 8 (SEQ ID NO: 33)).

Loops 1 and 4 are β-hairpins whilst loops 2 and 3 are β-links. The β-hairpins are more stable than the β-links and may therefore be more appropriate for fusion to longer peptide sequences. The β-links may be more suitable for fusion to peptides with extended conformation inserts.

The β2 microglobulin may be fused to a single peptide, or the β2 microglobulin may be fused to two or more peptides. Where two or more peptides are fused to the β2 microglobulin they may be located at one or more of the C-terminal end, N-terminal end or with one or more external loops of the β2 microglobulin.

If IVTT is used, it may be emulsion IVTT (Directed Evolution of Proteins In Vitro Using Compartmentalization in Emulsions Davidson, Dlugosz, Levy, Ellington, Current Protocols in Molecular Biology 24.6.1-24.6.12, July 2009) The peptide, and if applicable the β2 microglobulin, may be synthesised from DNA attached to the carrier. Preferably this is achieved using IVTT. The peptide, and if applicable the β2 microglobulin, may then be attached to the carrier. Alternatively, the peptide, and if applicable the β2 microglobulin, could be produced remote from the carrier and then attached to the carrier. The attachment may be covalent or non-covalent.

If produced by IVTT the peptide construct may also comprise a tag which attaches the peptide to the carrier. The tag may be a streptavidin binding protein, which when used in combination with a streptavidin coated/treated carrier attaches the peptide construct to the carrier. Alternatively a his-tag or HA-tag may be used. The skilled man will appreciate that these are merely examples and that other tags may be used.

Reference herein to a peptide construct is intended to refer to the product of the translation of a DNA molecule attached to the carrier, the construct may comprise the peptide and β2 microglobulin, a tag and a linker. The peptide construct may be attached to the carrier following emulsion PCR and emulsion IVTT. In this embodiment the DNA encoding the peptide and any other necessary components, for example one or more of a tag, β2 microglobulin, a linker, a promoter and a terminator, is first attached to the carrier by PCR. Preferably a primer for the DNA encoding the peptide and any other necessary components is first attached to the carrier, and PCR is then used to amplify the template DNA encoding the peptide and any other necessary components using the primer attached to the carrier. The DNA encoding the peptide may be randomly generated or derived from a source library for example a peptide human or non-human cell type. The primer may be attached to the carrier by any means known in the art. It may be bound covalently or non-covalently. DNA amplified by the PCR may be captured on the carrier. This may be achieved by using a tag on one of the primers, for example, the tag may be a biotin moiety and which would allow the amplified DNA to be captured on a streptavidin carrier. The primer carrying the tag may be the primer which is not bound to the carrier prior to PCR.

Preferably the PCR and/or the IVTT is carried out in an emulsion (as described in Directed Evolution of Proteins In Vitro Using Compartmentalization in Emulsions Davidson, Dlugosz, Levy, Ellington, Current Protocols in Molecular Biology 24.6.1-24.6.12, July 2009; Miniaturizing chemistry and biology in microdroplets. Kelly B T, Baret J C, Taly V, Griffiths A D. Chem Commun 2007 May 14; (18): 1773-88, the contents of which are hereby incorporated by reference). The emulsions may be made by stirring or agitating an oil and aqueous mixture to form small droplets of water in the oil. The emulsion may be stabilised by including a surfactant. Preferably where emulsion PCR and/or emulsion IVTT is carried out the carrier is a bead. Preferably each droplet in the emulsion contains only one bead. Preferably the aqueous phase of the emulsion carries all the reagents and enzymes necessary to carry out the PCR or the IVTT. For example, for a PCR reaction the aqueous phase preferably contains a DNA polymerase and nucleotides.

In order to move from an emulsion PCR reaction to an emulsion IVTT reaction the emulsion involved in the PCR reaction must be broken, the carrier (preferably beads) recovered, and then a new emulsion made with the carrier, IVTT reagents and enzymes. Emulsions can be broken or disrupted by any means known in the art. One well known method is to add more detergent/surfactant. If emulsion IVTT is performed and the carrier is a bead, preferably each bead has multiple copies of the encoding DNA attached to the bead. Preferably an individual bead has DNA of only one sequence attached. Preferably after IVTT each bead has multiple copies of the same DNA and the same peptide/protein product encoded by the DNA.

According to yet another aspect, the invention provides the use of a carrier according to the invention to identify a peptide ligand of a molecule, e.g. a receptor.

According to another aspect, the invention provides a method to identify a peptide ligand for a molecule, and/or the peptide ligand's encoding DNA, the method comprising providing a carrier or a library as described herein, and exposing the carrier or library to the molecule.

The configuration adopted on the carrier by the peptide and the β2 microglobulin preferably means that the peptide is presented in such a manner that it will be recognised by molecules of interest, e.g. receptors.

Preferably the method of the invention is performed in vitro.

By identifying a peptide ligand that is able to bind to a molecule, the DNA which encodes the peptide ligand recognised by the molecule can be readily recovered, amplified and sequenced. From the sequence of the DNA the protein from which the peptide is derived may be deduced.

The method of the invention has the advantage that it is very simple. Preferably it also has the advantage that it is free from interference by unwanted proteins, this is in contrast to phage display and the yeast two hybrid system where host proteins can interfere with the binding of the expressed peptide. Preferably the peptide, and the β2 microglobulin are the only proteins present on the carrier in the subject invention.

A further advantage of the invention is that the carrier may be multivalent, that is it may carry multiple copies of each peptide and its encoding DNA. This will increase the chance of interaction and also improve the rate of recovery.

Biological in vivo based systems (e.g. yeast or phage) can be limited in terms of library size because of limitations in handling large numbers of biological particles and efficient take up of library components. In contrast the in vitro system of the invention is not dependent on expression by yeast or phage and therefore can offer greater library sizes.

The method of the invention may further include the step of recovering the peptide, and/or its encoding DNA, which bound to a molecule. In a preferred embodiment the DNA encoding the peptide which bound to the molecule is recovered.

If the peptide is recovered it may be sequenced. The sequence may then be analysed to determine which protein the peptide is derived from, typically this is achieved using sequence databases.

If the nucleic acid encoding the peptide is recovered it may be sequenced. The sequence may than be analysed to determine the peptide it encodes and/or to determine the gene from which it is derived and/or to determine the protein from which the peptide it encodes is derived. The nucleic acid sequence may be determined through conventional Sanger based methodology or by using high throughput screening approaches. The advantage of high throughput screening approaches is that large numbers of sequences can be rapidly sequenced. Having obtained the sequence, either of the DNA encoding the peptide or the peptide itself, of one or more of the peptides that bind to a molecule, the sequences can then be compared to protein and DNA sequence databases to identify possible proteins or genes from which the peptide ligand is derived. Preferably the method will allow multiple different ligands to be identified which together will allow the protein from which they are derived to be identified.

To improve the analysis the molecules may first be probed with a carrier carrying peptide with a fixed sequence before probing with a peptide library. Bioinformatics could then be used to calculate a cut-off (based on the fixed sequence) above which non-fixed sequences may be relevant. The identified sequences could then be applied to database searches to examine common patterns that emerge. This system may be amenable to subsequent rounds of selection to enrich for sequences of interest. In addition the sequences generated in one round of selection can be used to derive a refined library for subsequent rounds of selection.

The β2 microglobulin is included to allow the peptide to be presented in the correct configuration such that it may be recognised by a molecule. β2 microglobulin is also known as B2M, and is present on virtually all nucleated cells. In humans, the β2 microglobulin protein is encoded by the B2M gene.

Preferably in the method of the invention the β2 microglobulin interacts with the peptide attached to the carrier to put the peptide into a confirmation such that it can be recognised by a molecule.

If the carrier is a bead the beads bound to a molecule, e.g. a receptor may be readily recovered by removing any unbound beads using size based exclusion or magnetic or fluorescence based cell sorting.

The molecules, e.g. receptors, used in the method of the invention may be provided as isolated proteins/receptors, and/or in membrane fragments, and/or on cells in mono culture, and/or in a mixed culture of cells, and/or in a mixed population of cells, such as found in a tissue sample. The tissue sample may have been homogenised to allow access to the component cells. The tissue sample may be a sample of normal or diseased or infected tissue.

Preferably each bead has multiple copies of the peptide and the DNA encoding the peptide attached. Preferably at least 10 copies, preferably at least 100 copies, preferably at least 1000 copies.

According to a further aspect the invention provides the use of peptide ligands, and/or the proteins from which they are derived, identified by the method of the invention, as a target for diagnostic, prognostic, therapeutic or preventative agents.

According to a further aspect the invention provides a kit for screening for a peptide ligand for a molecule, e.g. a receptor, wherein the kit comprises a carrier to which is attached a peptide, DNA encoding the peptide, and β2 microglobulin. The kit may also include instructions to expose the carrier to a molecule, e.g. a receptor and to isolate peptides, or the DNA encoding the peptides, that bind to the molecule. The β2 microglobulin may be provided attached to the carrier, or may be located at or near the carrier surface.

According to another aspect, the invention provides a method to identify a nucleotide sequence encoding a peptide that binds to a molecule, e.g. a receptor, comprising amplifying and sequencing the DNA attached to carrier carrying a peptide which binds to the molecule.

The skilled person will appreciate that all preferred features of the invention described with reference to only some aspects of the invention can be applied to all aspects of the invention. Preferred embodiments of the present invention will now be described, merely by way of example, with reference to the following drawings and examples.

In the Figures:

FIG. 1a shows an overview of a system for using the invention. Step 1: creation of $10^9$ beads, each bead is coated with homogenous DNA coding a unique peptide. A water-in-oil emulsion is formed for each bead, with each emulsion containing a single template with PCR components, generating bead-DNA complexes after PCR. Step 2: each bead-DNA complex forms a new emulsion with in vitro transcription/translation components for protein synthesis. Since the protein translated contains SBP, it will attach to the bead as soon as it is translated, resulting in the formation of a protein-DNA-bead complex. Step 3: the protein-DNA-bead complexes form a library of variable peptides, which are challenged with any protein of interest (e.g. gp120), the complexes will bind to the protein, and the encoding templates can be sequenced by conventional or next generation sequencing.

FIG. 1b shows the peptide library gene design. This 782 base-pair DNA template acts as the starting template for the synthesis of the randomised peptide library.

FIG. 2 shows post-emulsion PCR gel examinations performed with Dynabead C1. The DNA gel represents 8 independent emulsion PCR reactions. The emulsions were broken after PCR, and the DNA region containing random amino acids (approximately 450 bps, template=9 random amino acids) were amplified by standard PCR.

FIG. 3a shows emIVTT on different types of beads. Western blot results showing protein-DNA-beads attaching with either EBV BZLF1 positive control template (known peptide sequence) on upper row, or templates containing randomised peptide sequences (lower row). The left column shows the results of human β-2-microglobulin (β2m) staining and the right shows streptavidin-binding-protein staining. Each type of beads was labelled with three different concentrations biotin labelled primers attaching on the beads, e.g. for C1 column, 1000 pmol, 500 pmol, 250 pmol primers were attached on 1 mg of beads ($6-7 \times 10^7$).

FIG. 3b shows the 40× inverted microscopic image of a water-in-oil emulsion mixture with Dynabead C1. A successful water-in-oil emulsion has diameter of 10-15 μm and contains a single magnetic bead in the aqueous phase. The scale bar represents 20 μm.

FIG. 4 shows beads coated with β2m and the BZLF1 peptide refolded with recombinant HLA-B*0801 and stained for reactivity with W6/32 (a conformation dependent antibody).

FIG. 5a shows ELISA for the binding between predicted peptides and GP120 protein. Some predicted peptides (GP2, GP3, GP11, GP16) showed higher absorbance, i.e. peptides bind to GP120 in a dose-dependent manner, compared to the negative control (HA2, hemagglutinin-binding peptide). While most peptides bind to GP120 briefly, GP16 showed the highest binding affinity to GP120 among other peptides. (Paired t-test against negative controls, *p=0.02, p=0.003, *p=0.005; n=3)

FIG. 5b shows equilibrium dissociation constant $K_D$ calculation using surface plasmon resonance (SPR). An illustrated example of the $K_D$ calculation for GP16 peptide. The left of the figure is the non-linear fit of the Langmuir binding isotherm for GP16 binding. The table summarises the $K_D$ of the peptides tested.

FIG. 6 shows HIV-1 (HIV BAL, IIIB, clade C) inhibition assay. Peptides GP3, 5, 11, 16 were administered in 3 concentrations with or without streptavidin conjugation. T20 (Enfurvitide) was used as positive control.

Figures 9, 10:
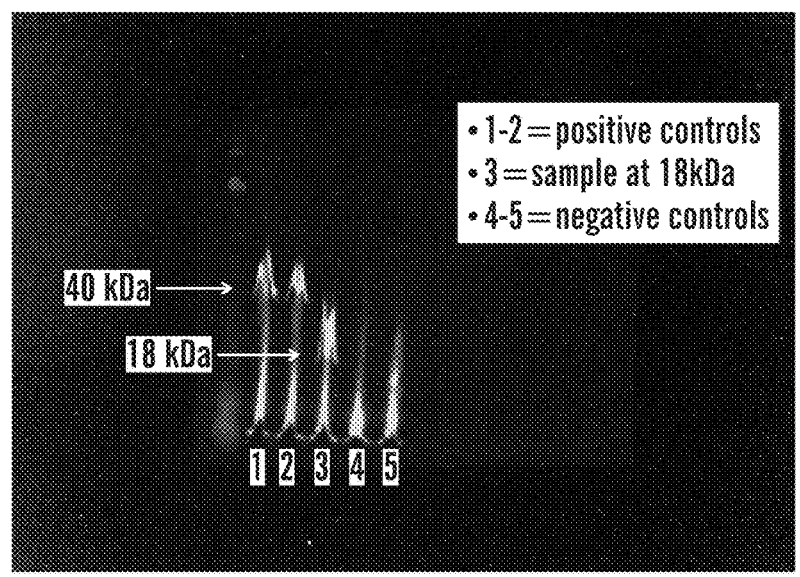

FIG. 9 demonstrates the incorporation of fluorescent non-natural amino acids in a peptide produced by IVTT and displayed on a bead.

FIG. 10 shows that disulphide bridges can be incorporated into peptides produced by IVTT and displayed on a bead.

The invention provides a novel multiplexed peptide expression and selection system (FIG. 1). The inventors have hypothesized that the use of a protein scaffold (β2-microglobulin) with known ability to deliver peptides to a tertiary molecule (HLA) would allow the presentation and screening of peptides that bind to target molecules of interest, even in the absence of HLA or HLA like molecules. Beta-2-microglobulin has a number of advantages as a carrier molecule including survival at the relatively low endosomal pH which may be important for screening peptides that might modify protein:protein interactions that occur in vivo at low pH.

The carrier of the invention is preferably a bead, and the bead system has a number of further advantages which have been found to be of value, including the ability to easily handle the beads for transfer to sequential binding steps with different conditions and requirements (e.g. positive/negative selection). For example, beads can be transferred sequentially to binding cells with different targets or conditions to select for beads with multiple characteristics without the need for bead re-derivation between each round of selection.

Example

Using HIV-1 gp120 as a model system, a small peptide library was screened for low affinity interactions with gp120. Peptides that despite low affinity could inhibit HIV-1 replication through blocking protein:protein interaction between gp120 and the co-receptor CCR5 were found.

Methods

Gp120 Synthesis

Gp120 was produced by transient transfection of 293T cells using the JRFL gp120—pLex construct. HIV-1 JRFL gp120 protein was captured from the supernatant by $Co^{2+}$ affinity chromatography to the C-terminal $his_6$ tag. The protein was further purified by size exclusion chromatography on a SD200 16/60 column and the protein purity was verified to be >98% pure by SDSPAGE. Conformation and binding function was confirmed by binding with recombinant human CD4 and a panel of HIV-1 Env-specific monoclonal antibodies in ELISA assays.

Beads Selection

Gp120 at a concentration of 100 μg/ml was coated to an immuno 96 micro-well plate (Nunc, UK) at 4° C. overnight.

After washing in PBST (0.05% Tween 20) 6 times, 50 µl PBS containing approximately 10 million beads collected after IVTT was added and incubated at 4° C. for 1 hr. After the incubation, the supernatant was collected and the wells were washed with PBST for 6 times. The beads which remained on the plate were then collected in TE buffer for subsequent PCR to pull down the DNA fragment containing the random nucleotide region.

Peptide Analysis and Synthesis

The sequence of 9 amino acids or 15 amino acids (cys) was translated from DNA sequencing data. The sequence analysis is performed with software R to characterise the frequency of different amino acids in each position and the frequency of 3 or longer amino-acid fragments. The sequences containing a high frequency of certain amino acids or fragments were chosen for synthesis. A GS-linker (GGGGSGG) and a biotin were added at the C terminal of the peptides. The purity was established by high-pressure liquid chromatography, and the individual peptides were dissolved at 20 mg/ml in dimethyl sulfoxide and diluted at 1 mg/ml with PBS.

Peptide Selection Via Amino Acid Sequence Analysis

The 9mer peptides were broken into 3mer fragments and the frequency of these 3mers was analysed with scripts written in R software. The peptides contain higher-frequency 3mers appeared in independent replicates were chosen to synthesis. For example, GP16 (LWCRRLNLL) was the peptide containing the NLL repeated for 6 times in 4 replicates and LWC repeated 2 times in 2 replicates.

ELISA (Antibody Blocking)

ELISA plate (Greiner, 655061) was coated with 1 µg/ml purified gp120 in PBS and incubated at 4° C. overnight. The plate was washed with ELISA wash buffer (PBS, 0.05% Tween20, VWR) followed by 100 µl blocking buffer (PBS, 0.05% Tween20, 2% BSA powder, Sigma) for 1 hr at room temperature. For antibody blocking experiment, V3/VRC01/F105 antibodies (NIBSC, CFAR3219/3291/3115) were used in 1 µg/ml for 1 hr at room temperature. After blocking, the plates were washed and peptides were added at different concentrations and incubate for 1 hr at room temperature. After washes, the detection of the binding was done by the addition of streptavidin conjugated peroxidase (Sigma, at 1:2500 dilution in PBS for 1 hr at room temperature and developed by TMB substrate (Thermo, 8008743723). After colour change was observed, stop buffer (0.16 M sulphuric acid, Sigma) was added to stop the reaction, and the absorbance was read at $OD_{450}$ with ELISA plate reader.

ELISA (Peptide Blocking)

JRFL gp120 protein was coated on ELISA plate at 1 µg/ml 4° C. overnight and blocking with BSA as described above. Peptides were prepared in 4 dilutions and added to the plate and incubated for 1 hr at room temperature. The plates were washed and recombinant CCR5 GST tag (H00001234-P01, ABNOVA) was added to the plate at 0.1 µg/ml and incubated for 1 hr at room temperature. The plates were washed and the detection antibody anti-GST HRP conjugated was added at 1:2000, 1 hr, room temperature. The developing process was identical as described above. Paired t-test was used to compare between different concentrations of peptides (GP1-22) and the negative control peptide (hemagglutinin-binding peptide, 9 amino acids) in the ELISA absorbance reading, 95% confidence level.

Surface Plasmon Resonance (BIAcore)

Ligand Immobilisation

Immobilisation of purified gp120 protein (1 mg/ml) and purified HLA-A2 heavy chain (reference control, 1 mg/ml) onto the surface of individual flow-cells (Fc1 and Fc2 respectively) of CM5 sensor chip (GE Healthcare) was performed under conditions of 20 µl/min flow rate and 25° C., with HBS-EP buffer (0.01 M HEPES pH 7.4, 0.15 M NaCl, 0.005% v/v Surfactant P20; GE Healthcare) as the running buffer. After initiating the system, 100 µl 0.05M solution of EDC [1-ethyl-3-(3-dimethylaminopropyl) carbodiimide]/NHS (N-Hydroxysuccinimide) at 1:1 ratio was injected to activate the dextran matrix of the sensor chip surface. After immobilisation, 150 µl of 1M ethanolamine hydrochloride was injected to deactivate the unreacted carboxylmethyl groups on the dextran matrix. Finally, 30 µl of Glycine pH2.5 was injected to remove any non-covalently bound proteins.

Measurement of the Binding Affinity of the Interaction Between Predicted Peptides and Gp120

The affinity analyses of the interaction between 9-amino-acid predicted peptides and purified gp120 were performed using the BIAcore T200 (GE Healthcare), under conditions of 10 µl/min flow rate and 25° C. and using HBS-EP buffer (0.01 M HEPES pH 7.4, 0.15 M NaCl, 0.005% v/v Surfactant P20; GE Healthcare) as the running buffer. Prior to experiment, the 9-amino-acid peptides were diluted to 1 mg/ml with HBS-EP buffer. A 2-fold serial dilution of totally 8 concentrations was used to pass through the immobilised peptides. The data were analysed using Microcal Origin version 7.5 (Microcal Software Limited).

HIV-1 Inhibition Assay

Intracellular p24 antigen expression in CD4+ cells were used to quantify HIV-1 infection. Viral inhibition was assessed by the HIV-1 infection rate after the peptide incubation. Cryopreserved PBMCs were thawed and stimulated with PHA (5 µg/mL) in RPMI 1640 medium (Sigma, UK) supplemented with 10% fetal calf serum (R10) for 3 days. Biotinylated peptides were incubated with streptavidin for 10 min in room temperature. The peptide tetramers (10 µM) and HIV-1$_{BaL}$ (National Institute for Biological Standards and Control, United Kingdom), HIV-1 IIIB and HIV-1 clade C (ES-X1936-C) were incubated at 37° C. for 30 min. Licensed HIV-1 fusion inhibitor T20 (5 µM) and HIV-1 without peptides were used as positive and negative controls. After the incubation, PBMCs were infected with HIV-1 isolates (with or without peptides incubation) at a multiplicity of infection (MOI) of 0.002. HIV-1-infected PBMC ($2 \times 10^5$) were cultured in triplicate in R10 with interleukin 2 (20 IU/mL) in 96-well round-bottomed plates. Cells were harvested at day 3, stained with Aqua Live/Dead Fixable stain (Invitrogen), fixed with 1% paraformaldehyde/20 µg/mL lysolecithin at RT, permeabilized with cold 50% methanol followed by 0.1% Nonidet P-40, finally stained with p24 antibody (KC-57-FITC; Beckman Coulter) and antibodies to CD3, CD4, and CD8 (conjugated to APC-Cy7, PE and APC, respectively; BD Biosciences) and analyzed by flow cytometry. HIV-1 infection rate was expressed as percentage of HIV-1-infected CD4+ T cells (identified by gating on CD3+CD8− cells, to allow for HIV-induced CD4 downregulation) and determined as follows: [(p24+, CD4+ T cells)+(p24+, CD4− T cells)]/[(p24+, CD4+ Tcells)+(p24+, CD4− T cells)+(P24−, CD4+ T cells)]×100. The protocols were described previously by Dorrell et al., Yang, H., et al., *Antiviral inhibitory capacity of CD8+ T cells predicts the rate of CD4+ T-cell decline in HIV-1 infection*. J Infect Dis, 2012. 206(4): p. 552-61.

Results

Library Structure and Generation

Figure 1A:
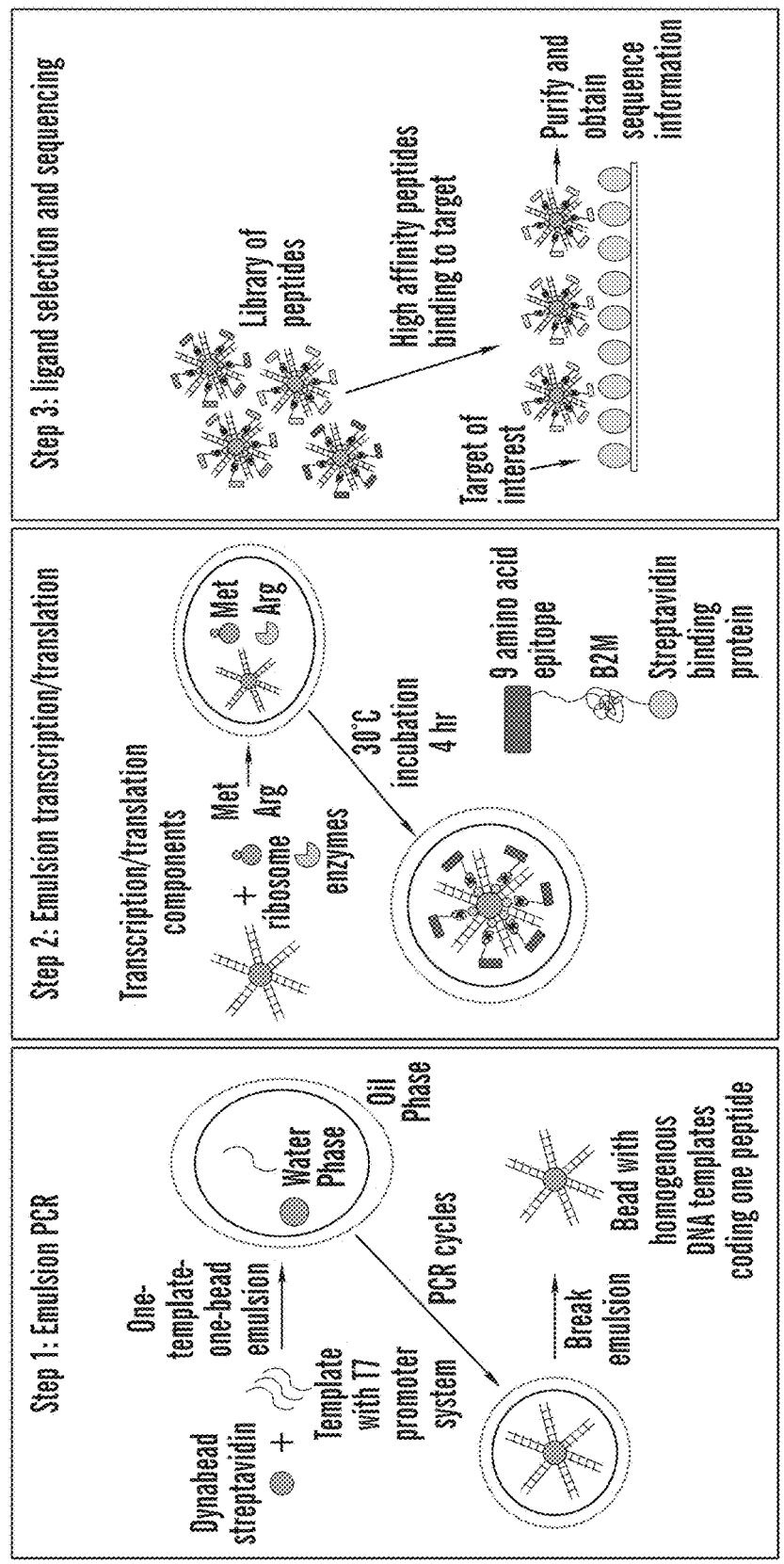

It was hypothesized that beta-2-microglobulin (β2m) would act as a good protein scaffold to present peptide on the surface of beads as it is known to be able to deliver peptides for binding to associated proteins (MHC). FIG. 1a shows a schematic of the bead structure and selection approach. Multiple DNA constructs with variant sizes of T7 promoter regions, peptide, linkers, β2-microglobulin and SBP (streptavidin—binding peptide) tag were tested (data not shown) but the positive control ("BZLF1" RAKFKQLL (SEQ ID NO: 1)) and the corresponding random construct in FIG. 1b proved to be optimal in terms of consistent expression. We used random peptide libraries containing nine and fifteen amino acids.

Figure 2:
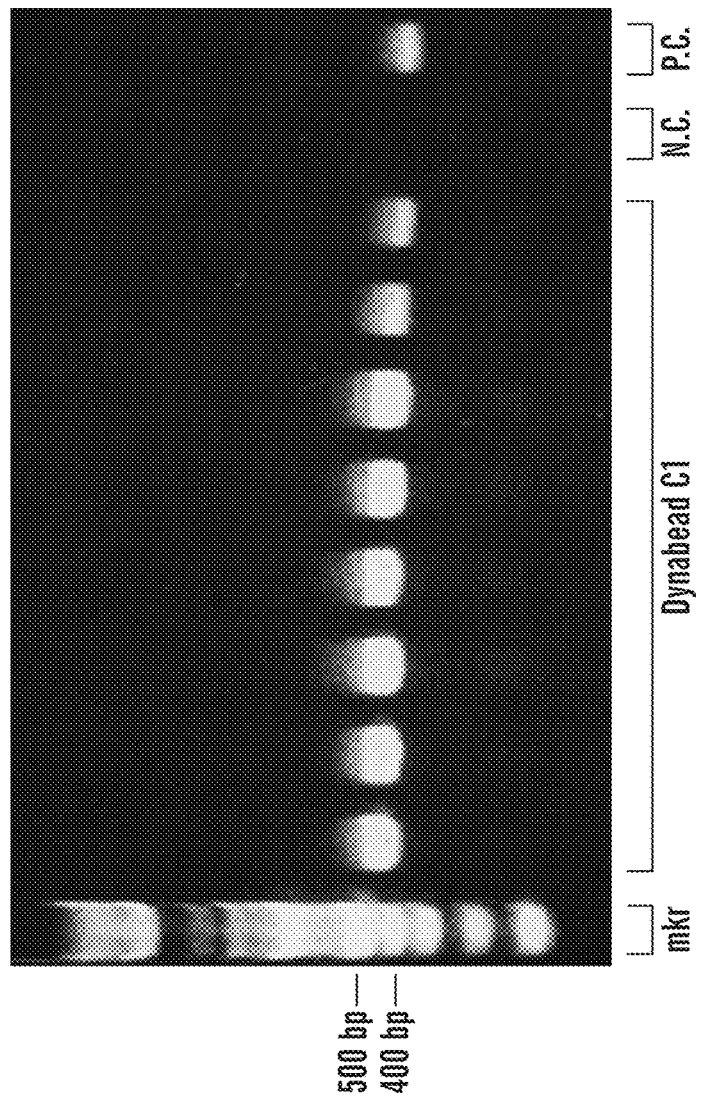

Emulsion PCR was undertaken using streptavidin magnetic beads labelled with biotinylated primers (forward primer: 5'-biotin-GATCTCGATCCCGCGAAATT (SEQ ID NO: 2); reverse primer: unmodified, 5'-TCCGGATATAGT-TCCTCCTT-3' (SEQ ID NO: 3)). The emulsion oil for each PCR reaction was prepared in a universal tube using ABIL EM90 and mineral oil. To equilibrate the emulsion oil, a magnetic stirrer (VWR UK) was used. Each aqueous PCR reaction (150 µl) was prepared as follows: 6 µl of primer-coupled beads, 3 µl of complement unmodified primers (400 µM), 3 µl of unmodified primer (2.5 µM), 3 µl of 10 mM PCR grade dNTPs, 4.5 µl of 50 mM MgCl$_2$, 10 µl of 20 µM DNA template, 15 µl 10×PCR buffer, and 9 µl of Taq DNA polymerase (5 U/µl). The water-in-oil emulsion was prepared by slow addition of the aqueous PCR mixture into the spinning emulsion oil. The emulsions were then aliquoted into 100 µl each, and PCR initiated. The emulsion was broken by adding 1 ml breaking buffer (10 mM Tris-HCl pH7.5, 1% Triton-X100, 1% SDS, 100 mM NaCl, 1 mM EDTA). Bead bound DNA could be detected by using magnetic bead separation from the supernatant and then PCR directly from the surface of the beads. FIG. 2 shows DNA product from 8 independent emulsion PCR products with Dynabead C1.

Figure 3A:
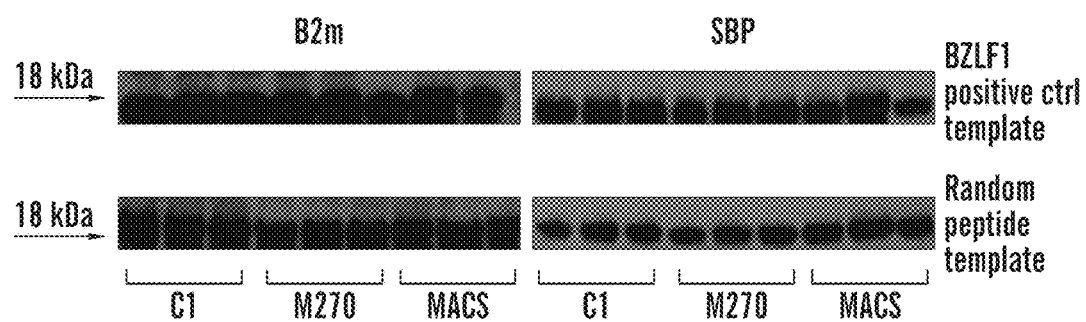
Figure 3B:
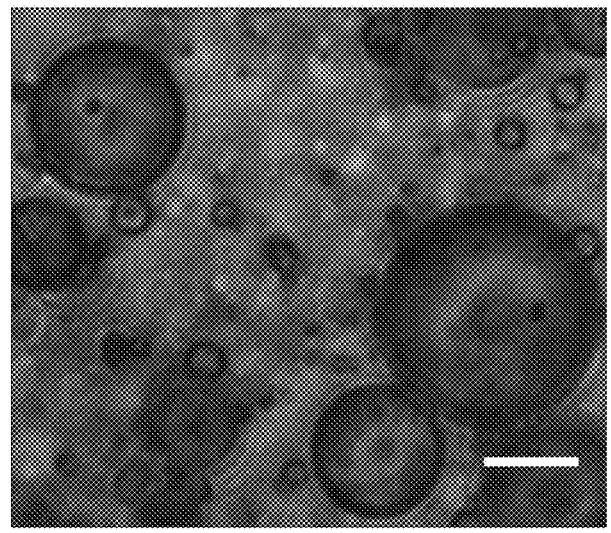

DNA-bound beads were then transferred to a new emulsion for in vitro transcription translation. Emulsion oils were prepared for a single reaction using mineral oil, Span-80, Tween-80, Triton X-100. Each in vitro transcription/translation reaction (IVTT) was prepared (RTS 100 E. coli, Roche) and the beads were added and mixed thoroughly before adding to the spinning emulsions as described above. The reaction was incubated at 30° C. for 4 hours and the emulsions broken as described above. The integrity of the translated proteins was examined by Western blot (FIG. 3a). Different bead sizes were tested and each showed successful expression of β2m and streptavidin binding peptide (SBP) epitopes, but with variable levels of expression (FIG. 3b). After the confirmation of the protein expression and ligation onto the beads, libraries of randomised 9/15-amino-acid peptides were generated.

Figure 4:
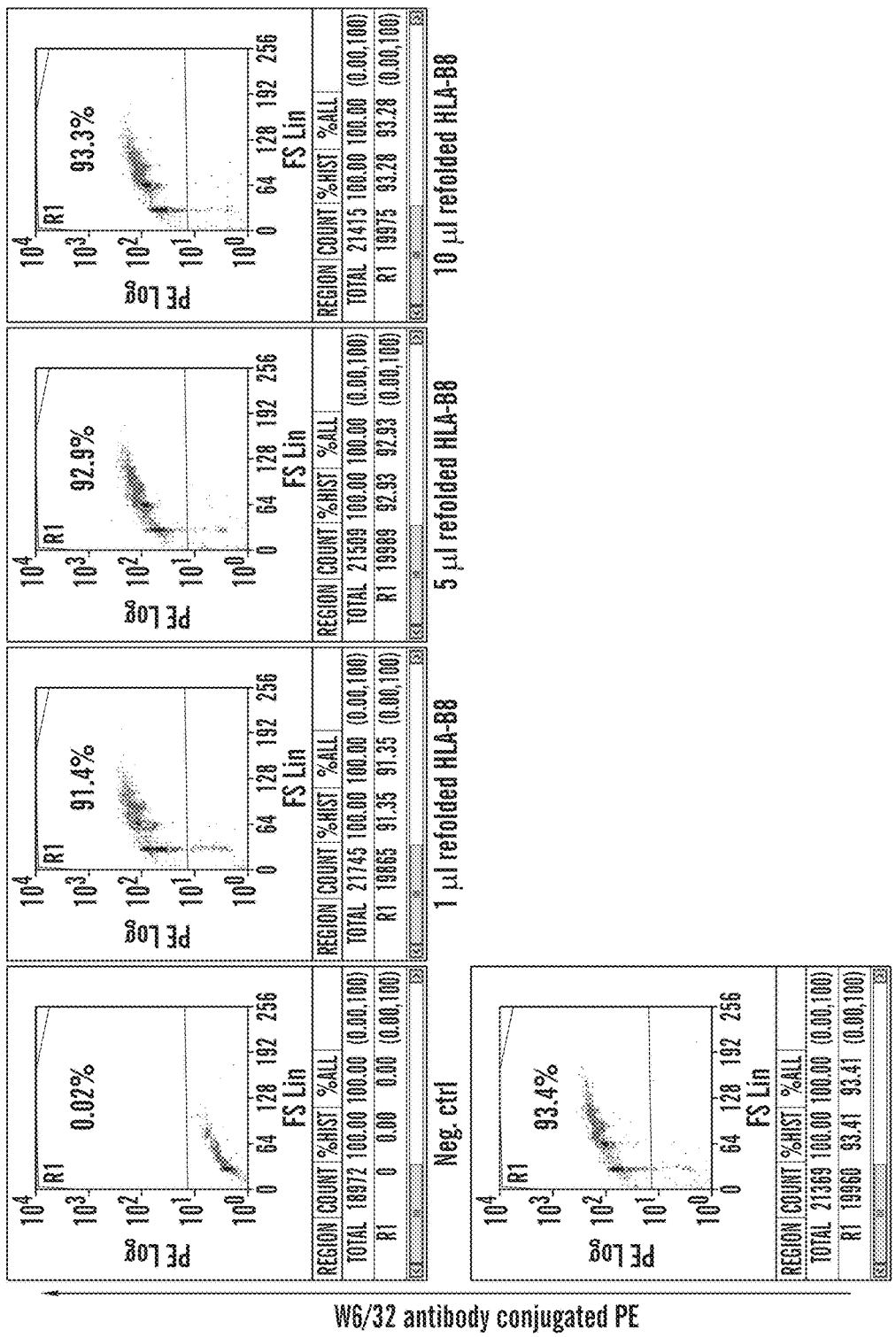

Beta-2-Microglobulin is Correctly Folded on the Bead Surface and Presents Peptides for Tertiary Interactions In order to confirm that the β2m was correctly refolded and able to present peptides for delivery to other molecules, we refolded the beads containing the fixed BZLF1 peptide (known HLA-B*0801 binding peptide) with exogenous HLA-B*0801 to generate the complete HLA, peptide, β2m complex on the surface of beads. As shown in FIG. 4, the beads were able to bind to W6/32 which is a conformationally dependent antibody. This suggests that the β2m is not only refolded correctly on the beads but that the peptide is available for interaction with tertiary molecules. To next confirm expression of the random library of peptides on the beads, we screened for binding partners of bovine serum albumin (BSA). 210 sequences were identified and five peptides were synthesized. All 5 peptides (Table 1) bound BSA on ELISA (FIG. 7) confirming that the random peptide library system was functional. We felt then able to proceed to identify peptides with potential biological function, using HIV-1 gp120 as the target.

TABLE 1

| peptide | sequence |
|---|---|
| BSA1 | L A V R K R M P H (SEQ ID NO: 4) |
| BSA2 | I T F D V Y K V A (SEQ ID NO: 5) |
| BSA3 | I A N G R H F Q H (SEQ ID NO: 6) |
| BSA4 | I R N Q D R C G L (SEQ ID NO: 7) |
| BSA5 | K V H S I M A W K (SEQ ID NO: 8) |
| BSA6 | V P L F K K Q F E (SEQ ID NO: 9) |

Figure 7:
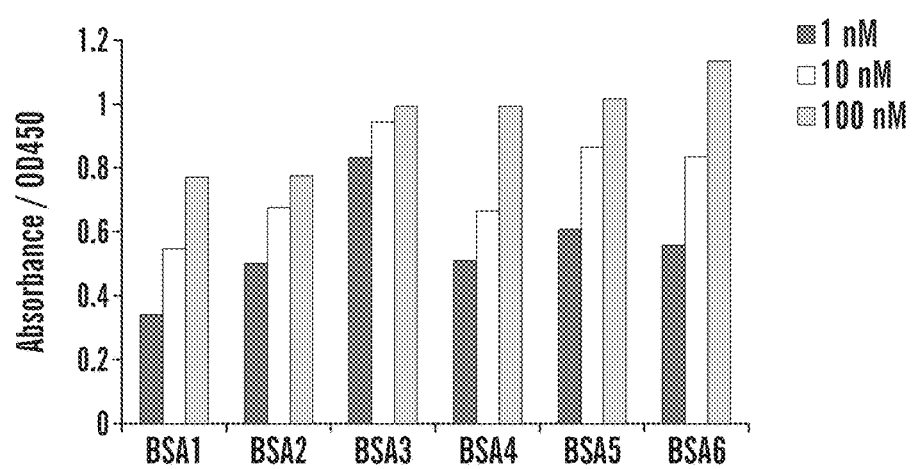
FIG. 7 shows binding of selected peptides (listed in Table 1) to BSA.
Figure 8:
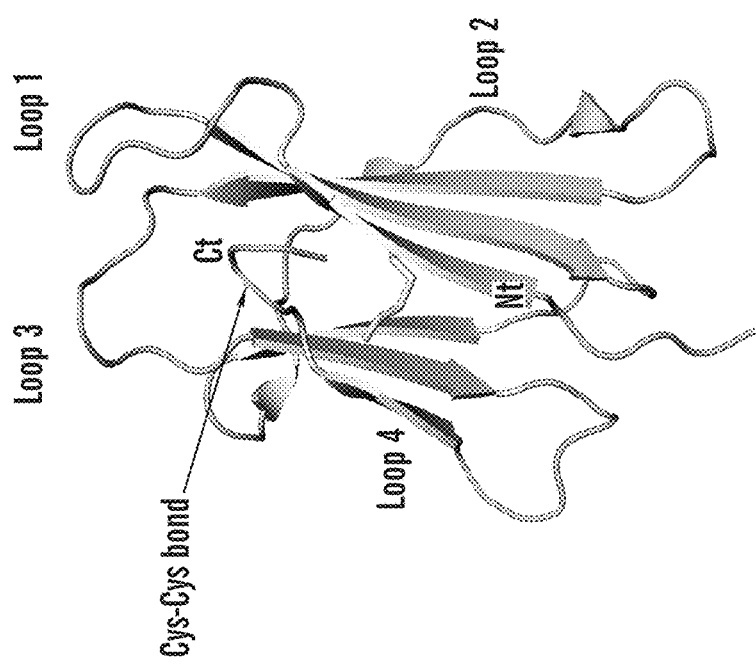
FIG. 8 shows schematically the structure of β2 microglobulin, and in particular highlights the loops that are externally located in the folded protein.
Figure 8:
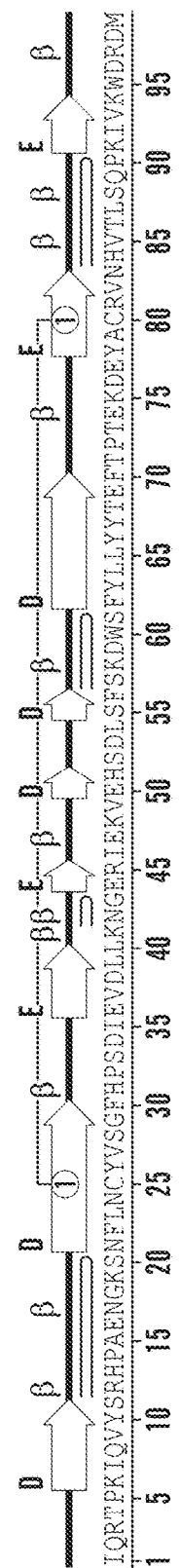

Peptides identified after selecting on bovine serum albumin were tested in ELISA and showed significant binding (see FIG. 7).

Validating the Binding of Predicted Peptides to Gp120

Having successfully generated the random peptide library on the surface of the beads together with the encoding DNA, we used the library to select peptides binding to HIV-1 viral coat protein gp120. After selection, the DNA templates of the beads remaining on the gp120-coated plate were amplified by PCR and the sequences of these peptides were obtained by sequencing. The most repeated peptide sequences are presented in Table 2 and show no similarities with the bovine serum albumin binding peptides (Table 1 above).

TABLE 2

| peptide | sequence | SEQ ID NO: |
|---|---|---|
| GP1 | MSTSCCLPS | (SEQ ID NO: 10) |
| GP2 | RRRNVPLIL | (SEQ ID NO: 11) |
| GP3 | SYSFCPRRQ | (SEQ ID NO: 12) |
| GP4 | AVNIVGYSN | (SEQ ID NO: 13) |
| GP5 | LVLLSSASS | (SEQ ID NO: 14) |
| GP6 | LRPLLSSMR | (SEQ ID NO: 15) |
| GP7 | LVLLLSSMS | (SEQ ID NO: 16) |
| GP8 | EMANRRSGS | (SEQ ID NO: 17) |
| GP9 | WFFTSLVTC | (SEQ ID NO: 18) |
| GP10 | SILSSCWQS | (SEQ ID NO: 19) |
| GP11 | LLALSAYMV | (SEQ ID NO: 20) |
| GP12 | RPLPILAPC | (SEQ ID NO: 21) |
| GP13 | GTRVFMRSL | (SEQ ID NO: 22) |
| GP14 | LSVLSRGML | (SEQ ID NO: 23) |
| GP15 | WHVLIWLLF | (SEQ ID NO: 24) |
| GP16 | LWCRRLNLL | (SEQ ID NO: 25) |
| GP17 | LWHTRRGPG | (SEQ ID NO: 26) |
| GP18 | SSCAGNLPREDQECC | (SEQ ID NO: 27) |
| GP19 | SSCQRLFVIAYPFKC | (SEQ ID NO: 28) |

TABLE 2-continued

| peptide | sequence | SEQ ID NO: |
|---|---|---|
| GP20 | SSCCFLPASWLKSLC | (SEQ ID NO: 29) |
| GP21 | SSCSVRSSCRLYYSC | (SEQ ID NO: 30) |
| GP22 | SSCLLFTSMLPDKTC | (SEQ ID NO: 31) |

Peptide sequences for 22 GP120-binding peptides selected by the method of the invention. All peptides have glycine-serine repeats (GGGGGGSGGSG) (SEQ ID NO: 32) at C-terminals for flexibility, followed by a lysine K residue for biotinylation.

Figure 5A:
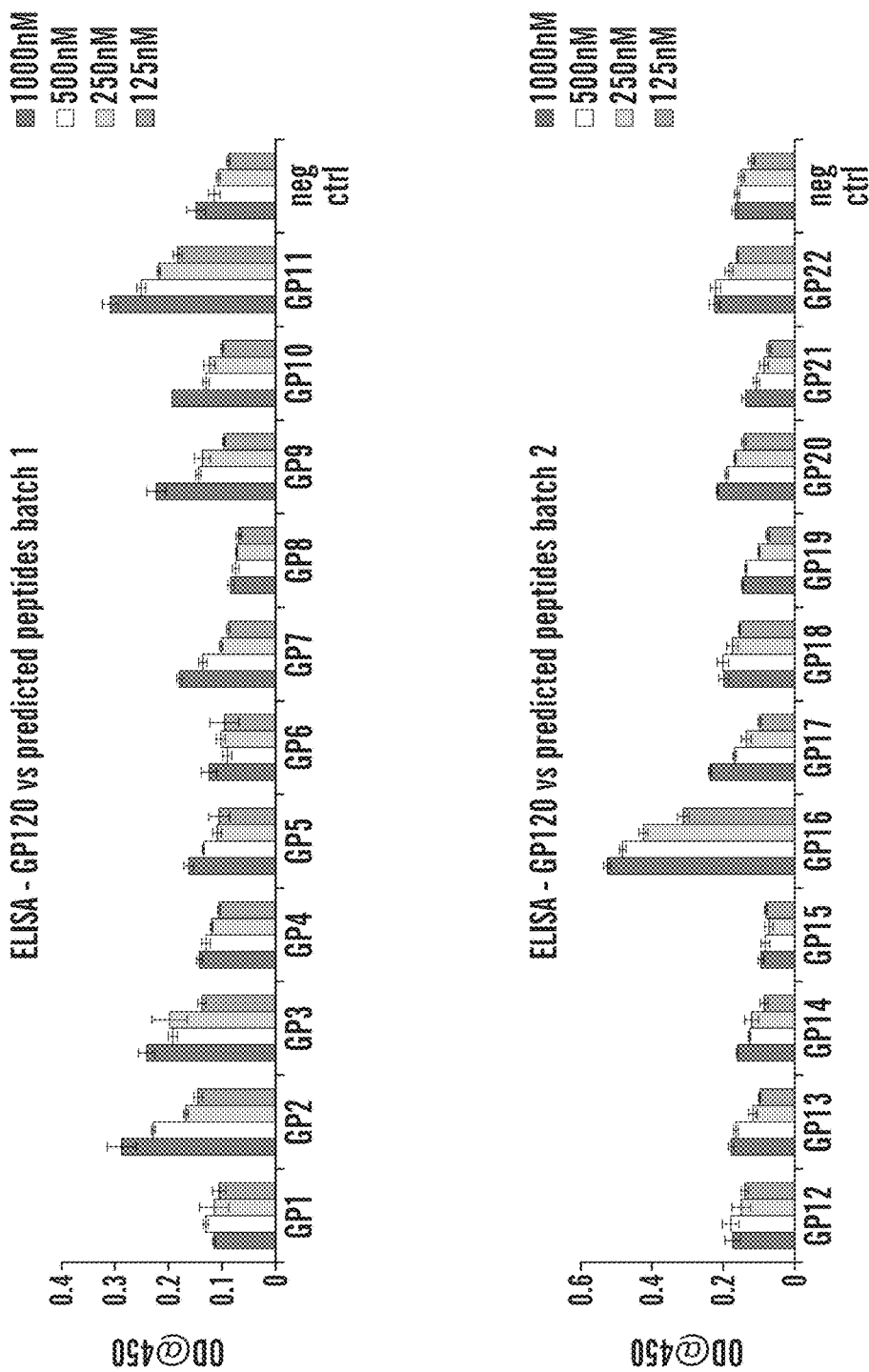

Highly ranked gp120-binding peptides were synthesised by F-moc chemistry with purity confirmed by HPLC. FIG. 5a showed the result of ELISA tests of the twenty two peptides. An irrelevant peptide was used as a reference for the peptides which has no binding to gp120. As shown in FIG. 5a, GP2, GP3, GP11 and GP16 had significantly higher binding to gp120 than the control hemagglutinin-binding peptide HA2 in a dose-dependent manner. However, while being a potentially useful screening tool, ELISA is susceptible to detection of non-specific and low affinity binding. We therefore proceeded to determine specific binding affinities using surface plasmon resonance.

Figure 5B:
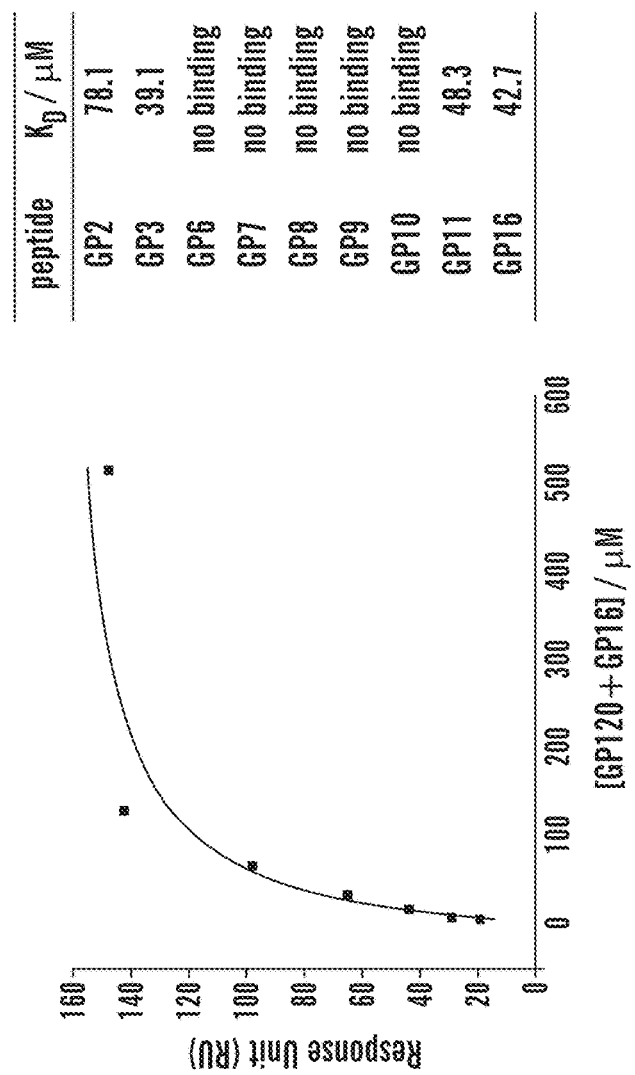

In order to obtain quantitative measurements of binding reactions between predicted peptides and gp120, surface plasmon resonance (BIAcore) was used to measure the equilibrium dissociation constant $K_D$ of the predicted peptides and gp120. Four peptides which showed higher absorbance in the ELISA experiments were selected for BIAcore experiments, together with five predicted to have intermediate or no binding from the ELISA. Since the $K_D$ to gp120 is relative to different analytes, purified protein HLA-A*0201 heavy chain was used as a reference control to measure the relative binding affinity of peptides to gp120. Purified gp120 and HLA-A*0201 were immobilised on chips, and the peptides were passed through both flow cells at a constant rate of 10 µl/min. FIG. 5b shows an illustrated example of the $K_D$ calculation for GP16 peptide and the $K_D$ for different peptides is shown in FIG. 5b. In general the peptides with positive binding on ELISA had a $K_D$ value ranging from approximately 20 to 80 µindicating that these peptides had the ability to bind gp120 protein, but with relative weak affinity. The BIcore experiment acted as a second confirmation that the randomised peptide library had successfully captured peptides which bind to gp120 in a single round of selection, and that the sequence information coding the binding peptides was correctly preserved and sequenced. Although binding affinity was in the micromolar range, we were aware that this was also the case of Enfuvirtide T20 which is a licensed therapeutic for HIV-1, and so proceeded to determine whether the peptides had HIV-1 replication inhibition activity either as monomers or as multimeric complexes.

HIV-1 Viral Inhibition with Streptavidin-Conjugated Peptides

Figure 6:
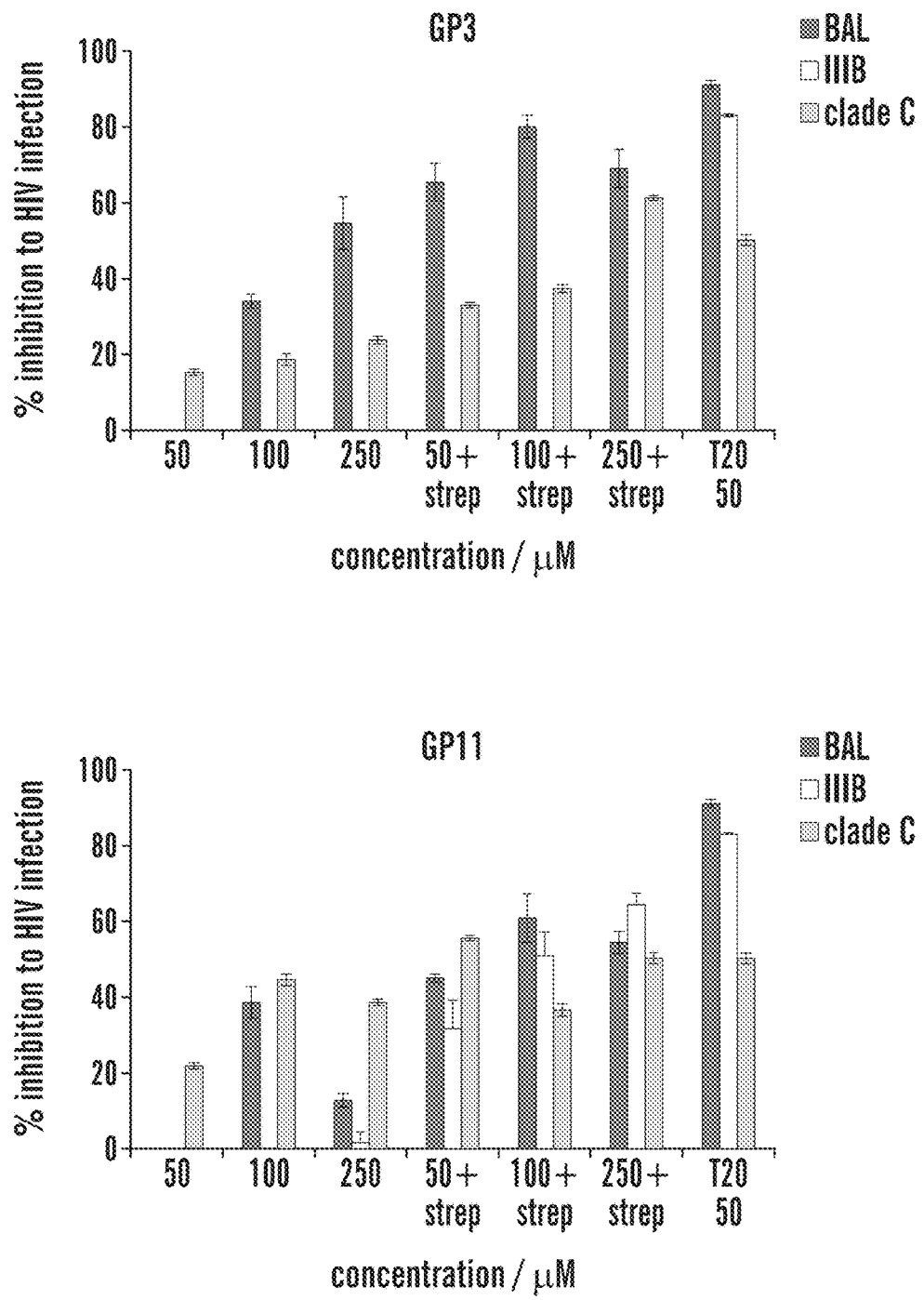
Figure 6:
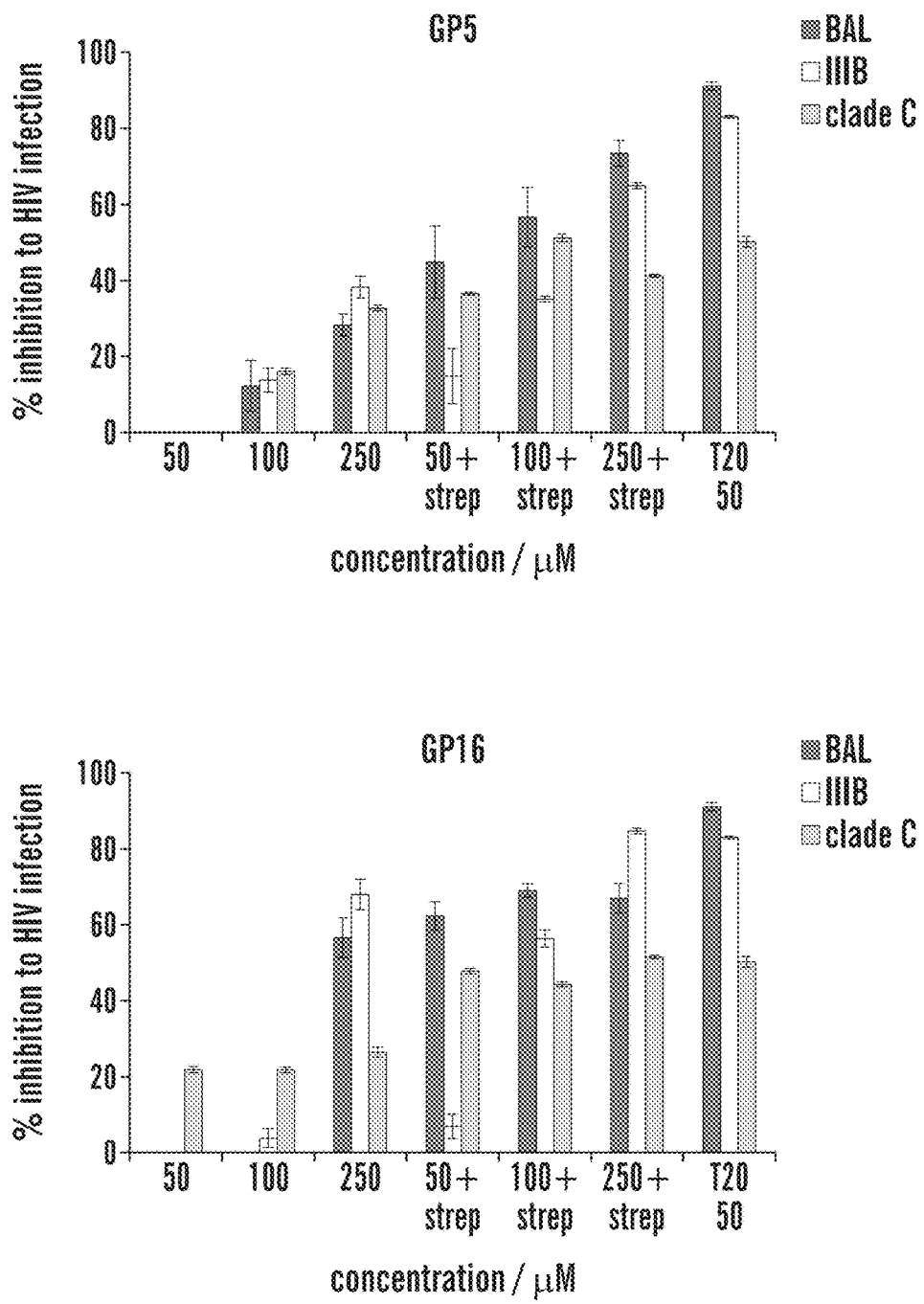

FIG. 6 shows the HIV-1 replication assay using biotinylated forms of the four peptides of highest affinity, with or without multiplexing using streptavidin conjugation (GP3, GP5, GP11, and GP16). In general, peptides administered directly without streptavidin conjugation had a very low inhibitory effect on HIV-1 replication, e.g. GP16 inhibited HIV-1 BaL infection by less than 1% at 50 and 100 μM, and 50% at 250 μM; GP3 had no inhibitory effect at 50 μM, and 34.5% and 54.7% inhibition at 100 μM and 250 μM respectively. Without streptavidin conjugation, peptides only exhibited viral inhibition at high concentration, and the effect was weak compared to the positive control Enfuvirtide (T20) (91.1% inhibition at 50 μM). When the streptavidin conjugated peptides were used, the inhibition was efficient and required concentrations comparable to Enfuvirtide T20, e.g. GP16 achieved 62.6% viral inhibition at 50 μM when conjugated with streptavidin. Similar patterns could be observed in different peptides and different HIV-1 clades. GP16, GP3 and GP11 exhibited cross clade HIV-1 inhibitory activity, and the effect was augmented with streptavidin conjugation. Of note, GP21 did not show any binding on ELISA and did not show any HIV-1 inhibition, consistent with the ELISA being useful screening tool for subsequent biological activity.

As gp120 is a highly polymorphic protein, HIV-1 neutralising antibodies are an invaluable tool to assess binding sites within the GP120 molecule. Three commercially available HIV-1 broadly neutralising antibodies V3 (anti-V3 447-52D, CCR5/CXCR4 binding sites), VRC01 (discontinuous CD4 binding site) and F105 (CD4 binding site) were prepared to test the binding sites of GP3 and GP16 peptides as these showed the greatest inhibition of HIV-1 replication. Peptide GP3 showed significant reduction ($p=0.025$) in absorbance when gp120 was pre-blocked with the V3 antibody, whereas GP16 had no reduction in gp120 blocked with any of the three antibodies, suggesting that GP16 bound to gp120 on other domains. Our data showed that peptide GP3 exhibited inhibition of replication of the HIV-1 clade C isolate and HIV-1 BaL, which are CCR5 tropic viruses; however no inhibition was observed when GP3 was co-incubated with HIV-1 IIIB, which is a CXCR4 tropic virus. This evidence suggested that peptide GP3 may be binding to gp120 CCR5 binding region. Indeed we observed a significant reduction in recombinant CCR5 binding to gp120 that had been pre-incubated with GP3 (65.8% reduction in absorbance at 125 ng peptide, $p=0.0038$)

Incorporation of Non-Natural Amino Acids

To demonstrate that non-natural amino acids can be incorporated into a peptide displayed on bead the non-natural amino acid kit "Clover Direct" was used. This kit, from Cosmobio J P, uses non-natural amino-acyl tRNA to recognize UAG codons and insert an non-natural amino acid conjugated to the fluorophore Hilyte Fluor 488 (which is similar to FITC). Hilyte Fluor 488 can be readily viusalised. To demonstrate that a peptide can be produced incorporating a non-natural amino acid by IVTT and displayed on a bead the following method was performed. The non-natural fluorescent aminoacyl-tRNA was centrifuged and then 10 μL of tRNA buffer was added to the non-natural aminoacyl-tRNA tube, and vortexed to dissolve completely. RNase-free water, template bound DNA beads, amino acids, methionine, and reaction mix were then mixed in a new 1.5 mL microcentrifuge tube. 10 μL of non-natural aminoacyl-tRNA solution and 100 μL of *E.coli* lysate was then added to the reaction mix. This was incubated at 30° C. for 0.5 to 2 hours to allow the IVTT reaction to proceed. The reaction was then stopped by placing the tube on ice, and fluorescent gel analysis was run at 488 nm as shown in FIG. 9. FIG. 9 shows in lane 3 that the fluorescent non-natural amino acid was incorporated into the peptide to produce a fluorescent band at the expected 18 kDa size.

Disulphide Bond Incorporation into a Peptide Displayed on a Bead

To demonstrate that a constrained peptide can be produced and displayed on a bead by IVTT, the IVTT reaction was performed using the 5 Prime RTS *E coli* disulphide kit. 15 μL of 4 mM cystamine working solution was added to each tube containing an IVTT reaction. A 0.6 mg/mL papain-SSCH$_3$ working solution was prepared and 0.5 mL was added to each assay tube and mixed well. The reactions were then incubated at room temperature for one hour. 0.5 mL of 4.9 mM L-BAPNA solution was then added to each assay tube and mixed well. To determine the presence of disulphide bonds the absorbance at 410 nm was measured. Experimental tubes were compared with the absorbance of standard curve solutions. The presence and amount of disulphide bonds was quantified using the Thiol and Sulfide Quantitation Kit (Molecular Probes) as described in the manufacturers' instructions. FIG. 10 illustrates that 1 or 2 disulphide bonds can be readily incorporated.

Discussion

The development and use of peptides as tools to target protein:protein interactions to probe biological processes or as the basis for future drugs or drug leads has been hampered by the lack of good cost-effective technologies to screen peptide libraries for binding activity. Conventional peptide libraries generated using F-moc chemistry are prohibitively expensive for library sizes of sufficient numbers required for drug discovery. Given that linear peptides will have relative low binding affinity, it is likely that multiplexing the peptides will be an important prerequisite for success. Of the existing systems of linking genotype:phenotype, only phage and yeast display can really achieve the levels of multiplicity required. However they too are not ideally suited for longer term systems of peptide library generation as they have associated problems of non-specific interactions with other coat proteins and are not easy to use with unnatural amino acids and for chemical modification before screening due phage/yeast toxicity. The invention provides in an aspect a novel in vitro bead display approach for displaying peptides using β2m as a scaffold structure. The use of β2m as a scaffold allows effective translation and delivery of linked peptides to tertiary molecules. The invention also provides a novel in vitro bead display approach for displaying peptides containing non-natural amino acids and/or constrained amino acids.

Further advantages of using an in vitro system include the possibility of using extremely large library sizes that are not limited by cloning efficiency into organisms. In vitro expression does not risk bias away from variants that confer growth disadvantage to particular phage or advantage to non-recombined phage. The beads may be simple, containing just peptide/protein and the encoding DNA; this means that there are fewer opportunities for non-specific interactions and that selection rounds can be reduced. Furthermore selection against a target can be undertaken in specific milieu that may not be possible using in vivo presentation, e.g. low pH that may be relevant for viral membrane fusion inhibitors or gastric environments for oral absorption. Lastly, beads are amenable to binding to targets on cells which adds further applications.

A binding system based on molecular interactions has been used to retain the selected beads. This has many advantages, as small numbers of beads can be selected from large libraries without dependence on threshold levels of fluorescence for detection which will be low for individual peptide:ligand interactions. Furthermore the beads can be readily isolated after each round of selection and transferred to sequential flow cells with different targets or conditions (e.g. target concentration, temperature, pH, buffer constituents) in order to undertake serial positive and/or negative selection to define multiple characteristics. Beads do not have to be re-derived between each sequential step and so even multiple selections can be undertaken quickly.

The peptides may be of value themselves, but in addition, they may provide structural data that is of value to the design of small drugs or other peptide mimetics. It is possible to use multiple rounds of selection to pick out peptides with higher affinity. Peptides (and peptide drug precursors) offer potential advantages over antibody approaches, as the inclusion of certain sequence and structural components can allow the absorption from the gut or lungs and the targeting of intracellular proteins as shown by ciclosporin. Lastly, peptides are readily amenable to multimerisation and modulation of pharmacokinetics such as through the use of pegylation with multiple peptide binding sites.

In summary, bead display of peptides using β2m as a scaffold base in accordance with the invention is a powerful approach to the identification of peptide ligands of disease relevant targets. The multiplex in vitro translation system is able to pick up low affinity peptides in a cost-effective approach. Although these peptides may be of value themselves, they can form the basis of further modifications or structural studies to inform the development of small drugs and other peptide mimetics for use to probe protein:protein interactions to understand biological process and for future therapeutic development.

Furthermore the bead display of peptides containing non-natural amino acids and/or having constrained structures may allow the production of more stable peptides and/or of peptides with higher binding affinities. Again, whilst the peptides may be of value themselves, they may also form the basis of further modifications or structural studies to inform the development of small drugs and other peptide mimetics for use to probe protein:protein interactions to understand biological process and for future therapeutic development.

The methods, uses and products as described herein by reference to the Examples is illustrative only and is not intended to limit the invention. Variations and alternatives will be apparent to the skilled person and should be construed as falling within the scope of the invention which is limited only by the claims.

In the above description of various features of the invention the skilled person will recognise that, unless mutually exclusive or technically unfeasible, combinations of each of the options for one feature may be made with each of the options for another feature. Accordingly, the various features may be combined mutatis mutandis to arrive at embodiments which have not been expressly recited.

The invention claimed is:

1. A carrier comprising:
   (a) multiple copies of a single peptide, wherein the copies are attached covalently or non-covalently to the surface of the carrier; and
   (b) multiple copies of the DNA that encodes the peptide of (a), wherein the copies of DNA are attached covalently or non-covalently to the surface of the carrier;
   wherein the copies of the peptide and the copies of the encoding DNA are attached to the carrier at separate sites such that the copies of the peptide and the copies of the DNA are not linked to each other,
   wherein the peptide includes at least one non-natural amino acid,
   and/or
   wherein the peptide has a constrained secondary structure.

2. The carrier of claim 1 wherein the peptide's secondary structure is constrained by at least one internal linkage between at least two amino acids of the peptide or wherein the peptide's secondary structure is constrained by binding to a scaffold molecule.

3. The carrier of claim 1, wherein β2 microglobulin is attached to the peptide.

4. The carrier of claim 1, further comprising a flexible linker attached to the peptide.

5. The carrier of claim 4, wherein the flexible linker is selected from the group consisting of β2 microglobulin, a His tag, a hapten, an epitope, a binding fragment of an antibody, or a member of a binding pair.

6. The carrier of claim 3, wherein the β2 microglobulin is attached to the peptide as part of a β2 microglobulin-peptide fusion, and the DNA encodes the β2 microglobulin-peptide fusion.

7. The carrier of claim 3 wherein the peptide is fused to the N-terminus, the C-terminus, or an internal site of β2 microglobulin.

8. The carrier of claim 7, wherein said β2 microglobulin-peptide fusion is attached to the carrier via an interaction between members of a binding pair of molecules, one of the members of the binding pair being attached to the peptide or fusion, and the second member of the binding pair being attached directly or indirectly to the carrier.

9. The carrier of claim 8, wherein the binding pair of molecules is streptavidin and a streptavidin binding protein.

10. The carrier of claim 8, wherein the binding pair of molecules is an antibody or binding fragment thereof, and its antigen or hapten.

11. The carrier of claim 10, wherein the antigen or hapten is attached to the peptide, β2 microglobulin-peptide fusion, or the carrier; and the antibody or binding fragment thereof is attached to the carrier, peptide or β2 microglobulin-peptide fusion.

12. The carrier of claim 11, wherein the carrier is multivalent.

13. The carrier of claim 11 wherein the peptide is between about 4 and about 50 amino acids and the carrier is a solid support.

14. A library containing a plurality of carriers of claim 1, wherein the library contains at least two different peptides borne on separate carriers.

15. The library of claim 14, wherein the at least two different peptides include a set of peptides in which at least one amino acid position is variable.

16. The library of claim 15, wherein non-natural amino acids or all natural amino acids are represented at the variable position.

17. A method to identify a peptide ligand for a molecule, and/or the peptide ligand's encoding DNA, the method comprising providing the library of claim 14 and exposing the library to the molecule.

18. The method of claim 17 further comprising the step of recovering the peptide ligand and/or its encoding DNA, from a carrier which bound to the molecule.

19. The method of claim 17 wherein a carrier which binds to the molecule is selected by binding to a solid support membrane, cell or lipid bilayer carrying the molecule.

20. The carrier of claim 1, wherein the carrier is a bead.

21. The carrier of claim 1, wherein said peptide is attached to the carrier via an interaction between members of a binding pair of molecules, one of the members of the binding pair being attached to the peptide, and the second member of the binding pair being attached directly or indirectly to the carrier.

22. The carrier of claim 21, wherein the binding pair of molecules is streptavidin and a streptavidin binding protein, or the binding pair of molecules is an antibody or binding fragment thereof, and its antigen or hapten.

\* \* \* \* \*

SEQUENCE LISTING

<160> NUMBER OF SEQ ID NOS: 33

<210> SEQ ID NO 1
<211> LENGTH: 8
<212> TYPE: PRT
<213> ORGANISM: Artificial Sequence

```
<220> FEATURE:
<223> OTHER INFORMATION: peptide

<400> SEQUENCE: 1

Arg Ala Lys Phe Lys Gln Leu Leu
1               5

<210> SEQ ID NO 2
<211> LENGTH: 20
<212> TYPE: DNA
<213> ORGANISM: Artificial Sequence
<220> FEATURE:
<223> OTHER INFORMATION: forward primer

<400> SEQUENCE: 2
gatctcgatc ccgcgaaatt                                                   20

<210> SEQ ID NO 3
<211> LENGTH: 20
<212> TYPE: DNA
<213> ORGANISM: Artificial Sequence
<220> FEATURE:
<223> OTHER INFORMATION: reverse primer

<400> SEQUENCE: 3
tccggatata gttcctcctt                                                   20

<210> SEQ ID NO 4
<211> LENGTH: 9
<212> TYPE: PRT
<213> ORGANISM: Artificial Sequence
<220> FEATURE:
<223> OTHER INFORMATION: peptide

<400> SEQUENCE: 4

Leu Ala Val Arg Lys Arg Met Pro His
1               5

<210> SEQ ID NO 5
<211> LENGTH: 9
<212> TYPE: PRT
<213> ORGANISM: Artificial Sequence
<220> FEATURE:
<223> OTHER INFORMATION: peptide

<400> SEQUENCE: 5

Ile Thr Phe Asp Val Tyr Lys Val Ala
1               5

<210> SEQ ID NO 6
<211> LENGTH: 9
<212> TYPE: PRT
<213> ORGANISM: Artificial Sequence
<220> FEATURE:
<223> OTHER INFORMATION: peptide

<400> SEQUENCE: 6

Ile Ala Asn Gly Arg His Phe Gln His
1               5

<210> SEQ ID NO 7
<211> LENGTH: 9
<212> TYPE: PRT
<213> ORGANISM: Artificial Sequence
<220> FEATURE:
<223> OTHER INFORMATION: peptide
```

```
<400> SEQUENCE: 7

Ile Arg Asn Gln Asp Arg Cys Gly Leu
1               5

<210> SEQ ID NO 8
<211> LENGTH: 9
<212> TYPE: PRT
<213> ORGANISM: Artificial Sequence
<220> FEATURE:
<223> OTHER INFORMATION: peptide

<400> SEQUENCE: 8

Lys Val His Ser Ile Met Ala Trp Lys
1               5

<210> SEQ ID NO 9
<211> LENGTH: 9
<212> TYPE: PRT
<213> ORGANISM: Artificial Sequence
<220> FEATURE:
<223> OTHER INFORMATION: peptide

<400> SEQUENCE: 9

Val Pro Leu Phe Lys Lys Gln Phe Glu
1               5

<210> SEQ ID NO 10
<211> LENGTH: 9
<212> TYPE: PRT
<213> ORGANISM: Artificial Sequence
<220> FEATURE:
<223> OTHER INFORMATION: peptide

<400> SEQUENCE: 10

Met Ser Thr Ser Cys Cys Leu Pro Ser
1               5

<210> SEQ ID NO 11
<211> LENGTH: 9
<212> TYPE: PRT
<213> ORGANISM: Artificial Sequence
<220> FEATURE:
<223> OTHER INFORMATION: peptide

<400> SEQUENCE: 11

Arg Arg Arg Asn Val Pro Leu Ile Leu
1               5

<210> SEQ ID NO 12
<211> LENGTH: 9
<212> TYPE: PRT
<213> ORGANISM: Artificial Sequence
<220> FEATURE:
<223> OTHER INFORMATION: Peptide

<400> SEQUENCE: 12

Ser Tyr Ser Phe Cys Pro Arg Arg Gln
1               5

<210> SEQ ID NO 13
<211> LENGTH: 9
<212> TYPE: PRT
<213> ORGANISM: Artificial Sequence
<220> FEATURE:
<223> OTHER INFORMATION: Peptide

<400> SEQUENCE: 13
```

Ala Val Asn Ile Val Gly Tyr Ser Asn
1               5

<210> SEQ ID NO 14
<211> LENGTH: 9
<212> TYPE: PRT
<213> ORGANISM: Artificial Sequence
<220> FEATURE:
<223> OTHER INFORMATION: Peptide

<400> SEQUENCE: 14

Leu Val Leu Leu Ser Ser Ala Ser Ser
1               5

<210> SEQ ID NO 15
<211> LENGTH: 9
<212> TYPE: PRT
<213> ORGANISM: Artificial Sequence
<220> FEATURE:
<223> OTHER INFORMATION: Peptide

<400> SEQUENCE: 15

Leu Arg Pro Leu Leu Ser Ser Met Arg
1               5

<210> SEQ ID NO 16
<211> LENGTH: 9
<212> TYPE: PRT
<213> ORGANISM: Artificial Sequence
<220> FEATURE:
<223> OTHER INFORMATION: Peptide

<400> SEQUENCE: 16

Leu Val Leu Leu Leu Ser Ser Met Ser
1               5

<210> SEQ ID NO 17
<211> LENGTH: 9
<212> TYPE: PRT
<213> ORGANISM: Artificial Sequence
<220> FEATURE:
<223> OTHER INFORMATION: Peptide

<400> SEQUENCE: 17

Glu Met Ala Asn Arg Arg Ser Gly Ser
1               5

<210> SEQ ID NO 18
<211> LENGTH: 9
<212> TYPE: PRT
<213> ORGANISM: Artificial Sequence
<220> FEATURE:
<223> OTHER INFORMATION: Peptide

<400> SEQUENCE: 18

Trp Phe Phe Thr Ser Leu Val Thr Cys
1               5

<210> SEQ ID NO 19
<211> LENGTH: 9
<212> TYPE: PRT
<213> ORGANISM: Artificial Sequence
<220> FEATURE:
<223> OTHER INFORMATION: Peptide

<400> SEQUENCE: 19

```
Ser Ile Leu Ser Ser Cys Trp Gln Ser
1               5

<210> SEQ ID NO 20
<211> LENGTH: 9
<212> TYPE: PRT
<213> ORGANISM: Artificial Sequence
<220> FEATURE:
<223> OTHER INFORMATION: Peptide

<400> SEQUENCE: 20

Leu Leu Ala Leu Ser Ala Tyr Met Val
1               5

<210> SEQ ID NO 21
<211> LENGTH: 9
<212> TYPE: PRT
<213> ORGANISM: Artificial Sequence
<220> FEATURE:
<223> OTHER INFORMATION: Peptide

<400> SEQUENCE: 21

Arg Pro Leu Pro Ile Leu Ala Pro Cys
1               5

<210> SEQ ID NO 22
<211> LENGTH: 9
<212> TYPE: PRT
<213> ORGANISM: Artificial Sequence
<220> FEATURE:
<223> OTHER INFORMATION: Peptide

<400> SEQUENCE: 22

Gly Thr Arg Val Phe Met Arg Ser Leu
1               5

<210> SEQ ID NO 23
<211> LENGTH: 9
<212> TYPE: PRT
<213> ORGANISM: Artificial Sequence
<220> FEATURE:
<223> OTHER INFORMATION: Peptide

<400> SEQUENCE: 23

Leu Ser Val Leu Ser Arg Gly Met Leu
1               5

<210> SEQ ID NO 24
<211> LENGTH: 9
<212> TYPE: PRT
<213> ORGANISM: Artificial Sequence
<220> FEATURE:
<223> OTHER INFORMATION: Peptide

<400> SEQUENCE: 24

Trp His Val Leu Ile Trp Leu Leu Phe
1               5

<210> SEQ ID NO 25
<211> LENGTH: 9
<212> TYPE: PRT
<213> ORGANISM: Artificial Sequence
<220> FEATURE:
<223> OTHER INFORMATION: Peptide

<400> SEQUENCE: 25

Leu Trp Cys Arg Arg Leu Asn Leu Leu
```

```
1               5

<210> SEQ ID NO 26
<211> LENGTH: 9
<212> TYPE: PRT
<213> ORGANISM: Artificial Sequence
<220> FEATURE:
<223> OTHER INFORMATION: Peptide

<400> SEQUENCE: 26

Leu Trp His Thr Arg Arg Gly Pro Gly
1               5

<210> SEQ ID NO 27
<211> LENGTH: 15
<212> TYPE: PRT
<213> ORGANISM: Artificial Sequence
<220> FEATURE:
<223> OTHER INFORMATION: Peptide

<400> SEQUENCE: 27

Ser Ser Cys Ala Gly Asn Leu Pro Arg Glu Asp Gln Glu Cys Cys
1               5                   10                  15

<210> SEQ ID NO 28
<211> LENGTH: 15
<212> TYPE: PRT
<213> ORGANISM: Artificial Sequence
<220> FEATURE:
<223> OTHER INFORMATION: Peptide

<400> SEQUENCE: 28

Ser Ser Cys Gln Arg Leu Phe Val Ile Ala Tyr Pro Phe Lys Cys
1               5                   10                  15

<210> SEQ ID NO 29
<211> LENGTH: 15
<212> TYPE: PRT
<213> ORGANISM: Artificial Sequence
<220> FEATURE:
<223> OTHER INFORMATION: Peptide

<400> SEQUENCE: 29

Ser Ser Cys Cys Phe Leu Pro Ala Ser Trp Leu Lys Ser Leu Cys
1               5                   10                  15

<210> SEQ ID NO 30
<211> LENGTH: 15
<212> TYPE: PRT
<213> ORGANISM: Artificial Sequence
<220> FEATURE:
<223> OTHER INFORMATION: Peptide

<400> SEQUENCE: 30

Ser Ser Cys Ser Val Arg Ser Ser Cys Arg Leu Tyr Tyr Ser Cys
1               5                   10                  15

<210> SEQ ID NO 31
<211> LENGTH: 15
<212> TYPE: PRT
<213> ORGANISM: Artificial Sequence
<220> FEATURE:
<223> OTHER INFORMATION: Peptide

<400> SEQUENCE: 31

Ser Ser Cys Leu Leu Phe Thr Ser Met Leu Pro Asp Lys Thr Cys
1               5                   10                  15
```

```
<210> SEQ ID NO 32
<211> LENGTH: 11
<212> TYPE: PRT
<213> ORGANISM: Artificial Sequence
<220> FEATURE:
<223> OTHER INFORMATION: peptide

<400> SEQUENCE: 32

Gly Gly Gly Gly Gly Gly Ser Gly Gly Ser Gly
1               5                   10

<210> SEQ ID NO 33
<211> LENGTH: 99
<212> TYPE: PRT
<213> ORGANISM: Homo sapiens

<400> SEQUENCE: 33

Ile Gln Arg Thr Pro Lys Ile Gln Val Tyr Ser Arg His Pro Ala Glu
1               5                   10                  15

Asn Gly Lys Ser Asn Phe Leu Asn Cys Tyr Val Ser Gly Phe His Pro
            20                  25                  30

Ser Asp Ile Glu Val Asp Leu Leu Lys Asn Gly Glu Arg Ile Glu Lys
        35                  40                  45

Val Glu His Ser Asp Leu Ser Phe Ser Lys Asp Trp Ser Phe Tyr Leu
    50                  55                  60

Leu Tyr Tyr Thr Glu Phe Thr Pro Thr Glu Lys Asp Glu Tyr Ala Cys
65                  70                  75                  80

Arg Val Asn His Val Thr Leu Ser Gln Pro Lys Ile Val Lys Trp Asp
                85                  90                  95

Arg Asp Met
```